(12) United States Patent
Kita et al.

(10) Patent No.: US 6,992,171 B2
(45) Date of Patent: Jan. 31, 2006

(54) POLYPEPTIDE AND ITS DNA

(75) Inventors: Shunbun Kita, Nishinomiya (JP); Yoshio Taniyama, Tsukuba (JP)

(73) Assignee: Takeda Pharmaceutical Company Limited, Osaka (JP)

(*) Notice: Subject to any disclaimer, the term of this patent is extended or adjusted under 35 U.S.C. 154(b) by 5 days.

(21) Appl. No.: 10/297,895

(22) PCT Filed: Jun. 20, 2001

(86) PCT No.: PCT/JP01/05258

§ 371 (c)(1),
(2), (4) Date: Dec. 10, 2002

(87) PCT Pub. No.: WO01/98341

PCT Pub. Date: Dec. 27, 2001

(65) Prior Publication Data

US 2003/0176339 A1 Sep. 18, 2003

(30) Foreign Application Priority Data

Jun. 22, 2000 (JP) ........................ 2000-188306
Apr. 20, 2001 (JP) ........................ 2001-122125

(51) Int. Cl.
  C07K 1/00    (2006.01)
  C07K 14/00   (2006.01)
  C07K 17/00   (2006.01)

(52) U.S. Cl. ................ 530/350; 435/69.1; 435/320.1; 514/12

(58) Field of Classification Search ............ 530/350; 514/12; 435/69.1, 7.1, 320.1, 325
See application file for complete search history.

(56) References Cited

FOREIGN PATENT DOCUMENTS

WO    WO 99/37757       7/1997
WO    PCT/US011/08631   * 3/2001

OTHER PUBLICATIONS

Birn, et al., Characterization of an epithelial approximately 460-kDa protein that facilitates endocytosis of intrinsic factor-vitamin B12 and binds receptor-associated protein.J Biol Chem. Oct. 17, 1997;272(42):26497–504.*
NCBI, AAC82612, intrinsic factor- from above publication.*

(Continued)

*Primary Examiner*—Robert A. Wax
*Assistant Examiner*—Robert B. Mondesi
(74) *Attorney, Agent, or Firm*—Elaine M. Ramesh; Mark Chao

(57) ABSTRACT

It is intended to construct a screening method, etc. for searching for compounds which are capable of binding to apolipoprotein A-I and thus promote or inhibit the binding of a cubulin fragment to apolipoprotein A-I, and provide preventives or remedies containing compounds obtained by the above screening method, etc. These compounds, etc. are usable in preventives and remedies for various diseases in which cubulin participates and the like.

2 Claims, 7 Drawing Sheets

```
MMNMSLPFLWSLLTLLIFAEVNGERGELELQRQKRSINLQQPRMATERGNLVFLTGSAQNIEFRTGSLGK
IKLNDEDLSECLHQIQKNKEDIIELKGSAIGLPQNISSQIYQLNSKLVDLERKFQGLQQTVDKKVCSSNP
CQNGGNCLNLHDSFFCICPPQWKGPLCSADVNECEIYSGTPLSCQNGGTCVNTMGSYSCHCPPETYGPQC
ASKYDDCEGGSVARCVHGICEDLMREQAGEPKYSCVCDAGWMSSPNSPACTLDRDECSFQPGPCSTLVQC
FNTQGSFYCGACPTGWQGNGYICEDINECEINNGGCSVAPPVECVNTPGSSHCQACPPGYQGDGRVCTLT
DICSVSNGGCHPDASCSSTLGSLPLCTCLPGYTGNGYGPNGCVQLSNICLSHPCLNGQCIDTVSGYFCKC
DSGWTGVNCTENINECLSNPCLNGGTCVDGVDSFSCECTRLWTGALCQVPQQVCGESLSGINGSFSYRSP
DVGYVHDVNCFWVIKTEMGKVLRITFTFFRLESMDNCPHEFLQVYDGDSSSAFQLGRFCGSSLPHELLSS
DNALYFHLYSEHLRNGRGFTVRWETQQPECCGILTGPYGSIKSPGYPGNYPPGRDCVWIVVTSPDLLVTF
TFGTLSLEHHDDCNKDYLEIRDGPLYQDPLLGKFCTTFSVPPLQTTGPFARIHFHSDSQISDQGFHITYL
TSPSDLRCGGNYTDPEGELFLPELSGPFTHTRQCVYMMKQPQGEQIQINFTHVELQCQSDSSQNYIEVRD
GETLLGKVCGNGTISHIKSITNSVWIRFKIDASVEKASFRAVYQVACGDELTGEGVIRSPFFPNVYPGER
TCRWTIHQPQSQVILLNFTVFEIGSSAHCETDYVEIGSSSILGSPENKKYCGTDIPSFITSVYNFLYVTF
VKSSSTENHGFMAKFSAEDLACGEILTESTGTIQSPGHPNVYPHGINCTWHILVQPNHLIHLMFETFHLE
FHYNCTNDYLEVYDTDSETSLGRYCGKSIPPSLTSSGNSLMLVFVTDSDLAYEGFLINYEAISAATACLQ
DYTDDLGTFTSPNFPNNYPNNWECIYRITVRTGQLIAVHFTNFSLEEAIGNYYTDFLEIRDGGYEKSPLL
GIFYGSNLPPTIISHSNKLWLKFKSDQIDTRSGFSAYWDGSSTGCGGNLTTSSGTFISPNYPMPYYHSSE
CYWWLKSSHGSAFELEFKDFHLEHHPNCTLDYLAVYDGPSSNSHLLTQLCGDEKPPLIRSSGDSMFIKLR
TDEGQQGRGFKAEYRQTCENVVIVNQTYGILESIGYPNPYSENQHCNWTIRATTGNTVNYTFLAFDLEHH
INCSTDYLELYDGPRQMGRYCGVDLPPPGSTTSSKLQVLLLTDGVGRREKGFQMQWFVYGCGGELSGATG
SFSSPGFPNRYPPNKECIWYIRTDPGSSIQLTIHDFDVEYHSRCNFDVLEIYGGPDFHSPRIAQLCTQRS
PENPMQVSSTGNELAIRFKTDLSINGRGFNASWQAVTGGCGGIFQAPSGEIHSPNYPSPYRSNTDCSWVI
RVDRYHRVLLNFTDFDLEPQDSCIMAYDGLSSTMSRLARTCGREQLANPIVSSGNSLFLRFQSGPSRQNR
GFRAQFRQACGGHILTSSFDTVSSPRFPANYPNNQNCSWIIQAQPPLNHITLSFTHFELERSTTCARDFV
EILDGGHEDAPLRCRYCGTDMPHPITSFSSALTLRFVSDSSISAGGFHTTVTASVSACGGTFYMAEGIFH
SPGYPDIYPPNVECVWNIISSPGNRLQLSFISFQLEDSQDCSRDFVEIREGNATGHLVGRYCGNSFPLNY
SSIVGHTLWVRFISDGSGSGTGFQATFMKIFGNDNIVGTHCKVASPFWPENYPHNSNYQWTVNVNASHVV
```

OTHER PUBLICATIONS

Moestrup et al. "The Intrinsic Factor–Vitamin B12 Receptor and Target of Teratogenic Antibodies is a Megalin–binding Peripheral Membrane Protein with Homology to Developmental Proteins" J. Biol. Chem. 273(9):5235–5242 (1998).

Kozyraki et al. "The Human Intrinsic Factor–Vitamin B12 Receptor, *Cubilin:* Molecular Characterization and Chromosomal Mapping of the Gene to 10p Within the Autosomal Recessive Megalobastic Anemia (MGA1) Region" *Blood* 91(10): 3593–3600 (1998).

Hammad et al. "Cubilin, the endocytic receptor for intrinsic factor–vitamin B12 complex, mediates high–density lipoprotein holoparticle endocytosis" PNAS(USA) 96:10158–10163 (1999).

Kozyraki et al. "The intrinsic factor–vitamin B12 receptor, *cublin,* is a high–affinity apolipoprotein A–1 receptor facilitating endocytosis of high–density lipoprotein" Nature Medicine 5(6): 656–661 (1999).

Kristiansen et al. "Molecular Dissection of the Intrinsic Factor–Vitamin B12 Receptor, Cubilin, Discloses Regions Important for Membrane Association and Ligand Binding" J. Biol. Chem. 274(29):20540–20544 (1999).

* cited by examiner

Fig. 1

MMNMSLPFLWSLLTLLIFAEVNGERGELELQRQKRSINLQQPRMATERGNLVFLTGSAQNIEFRTGSLGK
IKLNDEDLSECLHQIQKNKEDIIELKGSAIGLPQNISSQIYQLNSKLVDLERKFQGLQQTVDKKVCSSNP
CQNGGNCLNLHDSFFCICPPQWKGPLCSADVNECEIYSGTPLSCQNGGTCVNTMGSYSCHCPPETYGPQC
ASKYDDCEGGSVARCVHGICEDLMREQAGEPKYSCVCDAGWMSSPNSPACTLDRDECSFQPGPCSTLVQC
FNTQGSFYCGACPTGWQGNGYICEDINECEINNGGCSVAPPVECVNTPGSSHCQACPPGYQGDGRVCTLT
DICSVSNGGCHPDASCSSTLGSLPLCTCLPGYTGNGYGPNGCVQLSNICLSHPCLNGQCIDTVSGYFCKC
DSGWTGVNCTENINECLSNPCLNGGTCVDGVDSFSCECTRLWTGALCQVPQQVCGESLSGINGSFSYRSP
DVGYVHDVNCFWVIKTEMGKVLRITFTFFRLESMDNCPHEFLQVYDGDSSSAFQLGRFCGSSLPHELLSS
DNALYFHLYSEHLRNGRGFTVRWETQQPECGGILTGPYGSIKSPGYPGNYPPGRDCVWIVVTSPDLLVTF
TFGTLSLEHHDDCNKDYLEIRDGPLYQDPLLGKFCTTFSVPPLQTTGPFARIHFHSDSQISDQGFHITYL
TSPSDLRCGGNYTDPEGELFLPELSGPFTHTRQCVYMMKQPQGEQIQINFTHVELQCQSDSSQNYIEVRD
GETLLGKVCGNGTISHIKSITNSVWIRFKIDASVEKASFRAVYQVACGDELTGEGVIRSPFFPNVYPGER
TCRWTIHQPQSQVILLNFTVFEIGSSAHCETDYVEIGSSSILGSPENKKYCGTDIPSFITSVYNFLYVTF
VKSSSTENHGFMAKFSAEDLACGEILTESTGTIQSPGHPNVYPHGINCTWHILVQPNHLIHLMFETFHLE
FHYNCTNDYLEVYDTDSETSLGRYCGKSIPPSLTSSGNSLMLVFVTDSDLAYEGFLINYEAISAATACLQ
DYTDDLGTFTSPNFPNNYPNNWECIYRITVRTGQLIAVHFTNFSLEEAIGNYYTDFLEIRDGGYEKSPLL
GIFYGSNLPPTIISHSNKLWLKFKSDQIDTRSGFSAYWDGSSTGCGGNLTTSSGTFISPNYPMPYYHSSE
CYWWLKSSHGSAFELEFKDFHLEHHPNCTLDYLAVYDGPSSNSHLLTQLCGDEKPPLIRSSGDSMFIKLR
TDEGQQGRGFKAEYRQTCENVVIVNQTYGILESIGYPNPYSENQHCNWTIRATTGNTVNYTFLAFDLEHH
INCSTDYLELYDGPRQMGRYCGVDLPPPGSTTSSKLQVLLLTDGVGRREKGFQMQWFVYGCGGELSGATG
SFSSPGFPNRYPPNKECIWYIRTDPGSSIQLTIHDFDVEYHSRCNFDVLEIYGGPDFHSPRIAQLCTQRS
PENPMQVSSTGNELAIRFKTDLSINGRGFNASWQAVTGGCGGIFQAPSGEIHSPNYPSPYRSNTDCSWVI
RVDRYHRVLLNFTDFDLEPQDSCIMAYDGLSSTMSRLARTCGREQLANPIVSSGNSLFLRFQSGPSRQNR
GFRAQFRQACGGHILTSSFDTVSSPRFPANYPNNQNCSWIIQAQPPLNHITLSFTHFELERSTTCARDFV
EILDGGHEDAPLRGRYCGTDMPHPITSFSSALTLRFVSDSSISAGGFHTTVTASVSACGGTFYMAEGIFN
SPGYPDIYPPNVECVWNIISSPGNRLQLSFISFQLEDSQDCSRDFVEIREGNATGHLVGRYCGNSFPLNY
SSIVGHTLWVRFISDGSGSGTGFQATFMKIFGNDNIVGTHGKVASPFWPENYPHNSNYQWTVNVNASHVV

Fig. 2

```
HGRILEMDIEEIQNCYYDKLRIYDGPSIHARLIGAYCGTQTESFSSTGNSLTFHFYSDSSISGKGFLLEW
FAVDAPDGVLPTIAPGACGGFLRTGDAPVFLFSPGWPDSYSNRVDCTWLIQAPDSTVELNILSLDIESHR
TCAYDSLVIRDGDNNLAQQLAVLCGREIPGPIRSTGEYMFIRFTSDSSVTRAGFNASFHKSCGGYLHADR
GIITSPKYPETYPSNLNCSWHVLVQSGLTIAVHFEQPFQIPNGDSSCNQGDYLVLRNGPDIYSPPLGPPG
CNGHFCGSHASSTLFTSDNQMFVQFISDHSNEGQGFKIKYEAKSLACGGNVYIHDADSAGYVTSPNHPHN
YPPHADCIWILAAPPETRIQLQFEDRFDIEVTPNCTSNYLELRDGVDSDAPILSKFCGTSLPSSQWSSGE
VMYLRFRSDNSPTHVGFKAKYSIAQCGGRVPGQSGVVESIGHPTLPYRDNLFCEWHLQGLSGHYLTISFE
DFNLQNSSGCEKDFVEIWDNHTSGNILGRYCGNTIPDSIDTSSNTAVVRFVTDGSVTASGFRLRFESSME
ECGGDLQGSIGTFTSPNYPNPNPHGRICEWRITAPEGRRITLMFNNLRLATHPSCNNEHVIVFNGIRSNS
PQLEKLCSSVNVSNEIKSSGNTMKVIFFTDGSRPYGGFTASYTSSEDAVCGGSLPNTPEGNFTSPGYDGV
RNYSRNLNCEWTLSNPNQGNSSISIHFEDFYLESHQDCQFDVLEFRVGDADGPLMWRLCGPSKPTLPLVI
PYSQVWIHFVTNERVEHIGFHAKYSFTDCGGIQIGDSGVITSPNYPNAYDSLTHCSWLLEAPQGHTITLT
FSDFDIEPHTTCAWDSVTVRNGGSPESPIIGQYCGNSNPRTIQSGSNQLVVTFNSDHSLQGGGFYATWNT
QTLGCCGIFHSDNGTIRSPHWPQNFPENSRCSWTAITHKSKHLEISFDNNFLIPSGDGQCQNSFVKVWAG
TEEVDKALLATGCCGNVAPGPVITPSNTFTAVFQSQEAPAQGFSASFVSRCGSNFTGPSGYIISPNYPKQY
DNNMNCTYVIEANPLSVVLLTFVSFHLEARSAVTGSCVNDGVHIIRGYSVMSTPFATVCGDEMPAPLTIA
GPVLLNFYSNEQITDFGFKFSYRIISCGGVFNFSSGIITSPAYSYADYPNDMHCLYTITVSDDKVIELKF
SDFDVVPSTSCSHDYLAIYDGANTSDPLLGKFCGSKRPPNVKSSNNSMLLVFKTDSFQTAKGWKMSFRQT
LGPQQGCGGYLTGSNNTFASPDSDSNGMYDKNLNCVWIIIAPVNKVIHLTFNTFALEAASTRQRCLYDYV
KLYDGDSENANLAGTFCGSTVPAPFISSGNFLTVQFISDLTLEREGFNATYTIMDMPCGGTYNATWTPQN
ISSPNSSDPDVPFSICTWVIDSPPHQQVKITVWALQLTSQDCTQNYLQLQDSPQGHGNSRFQFCGRNASA
VPVFYSSMSTAMVIFKSGVVNRNSRMSFTYQIADCNRDYHKAFGNLRSPGWPDNYDNDKDCTVTLTAPQN
HTISLFFHSLGIENSVECRNDFLEVRNGSNSNSPLLGKYCGTLLPNPVFSQNNELYLRFKSDSVTSDRGY
EIIWTSSPSGCGGTLYGDRGSFTSPGYPGTYPNNTYCEWVLVAPAGRLVTINFYFISIDDPGDCVQNYLT
LYDGPNASSPSSGPYCGGDTSIAPFVASSNQVFIKFHADYARRPSAFRLTWDS
```

POLYPEPTIDE AND ITS DNA

TECHNICAL FIELD

The present invention relates to partial peptides of cubilin and their functions.

BACKGROUND ART

The level of HDL-cholesterol [cholesterol contained in HDL (high density lipoprotein); hereinafter, sometimes abbreviated to "HDL-C"] is known as a negative risk factor in coronary artery diseases. Various drugs has been developed for the purpose of raising that level, but thus developed drugs, such as fibrate type drugs, are not sufficient though they raise HDL-C levels significantly. Besides, such rise in HDL-C levels represents a consequential factor. Recent studies using transgenic mice, etc. have revealed that, as long as the true purpose is to extract cholesterol from foci of arteriosclerosis, what is needed is technology to raise the level of apolipoprotein A-I (hereinafter, sometimes abbreviated to "apo A-I") that plays a major role in the cholesterol extraction.

Apo A-I in plasma exists for the most part as HDL in the form of complexes with phospholipid, cholesterol, cholesterol ester and so on. These complexes are catabolized mainly in the liver. However, it is known that in some diseases such as hypertriglyceridemia, HDL particles with increased triglyceride (hereinafter, sometimes abbreviated to "TG") contents are converted into smaller apo A-I particles by various lipases and then catabolized mainly in the kidney. The catabolism in the kidney is achieved as follows: small particles of apo A-I that have been filtered through the uriniferous tubule are re-absorbed in the proximal tubule and then degraded. Kozyraki et al. have been reported that cubilin (GenBank Accession No. AF034611) molecules expressed on the uriniferous tubule epithelium and known to bind to vitamin $B_{12}$-intrinsic factor complex and LDL receptor-related protein (LRP)-associated protein (hereinafter, sometimes abbreviated to "RAP") also bind to apo A-I (see, for example, Nature Medicine Vol. 5, No. 6, 656–661 (1999); Proc. Natl. Acad. Sci. USA, Vol. 96, 10158–10163 (1999)). However, relations between the binding of cubilin to apo A-I and plasma apo A-I or HDL concentration, or relations between this binding and arteriosclerosis have not yet been elucidated.

The binding of cubilin to apo A-I may be an important finding for the development of therapeutics for hypo-high density lipoproteinemia, which is a problem in diseases such as high hypertriglyceridemia, and for the development of drugs for treating arteriosclerosis at the root. To specify the apo A-I-binding domain in cubilin molecules is extremely useful, for example, for developing anti-cubilin-apo A-I-binding domain antibody and screening for certain low molecular weight compounds.

Thus, the finding that the apo A-I-binding site is located in a specific region in cubilin molecules is extremely important in view of clinical application, and the identification of this binding site has been eagerly awaited. Furthermore, the raising of serum apo A-I concentration and HDL concentration by administering a substance that inhibits the binding of apo A-I to cubilin partial fragments, and therapeutics for arteriosclerosis comprising such a substance have been eagerly awaited in order to treat hypertriglyceridemia, hypercholesterolemia and arteriosclerotic diseases.

DISCLOSURE OF THE INVENTION

The present invention provides the identification of the apo A-I-binding site on cubilin; the construction of a screening method for a compound that inhibits the binding of a cubilin fragrant comprising the identified binding site to apo A-I; and a medicine comprising a compound obtained by the constructed screening method.

To specify the apo A-I-binding site in cubilin molecules leads to clinical application of apo A-I-binding fragments of cubilin per se, antibodies thereto, and low molecular weight compounds that inhibit the binding of cubilin fragments to apo A-I.

As a result of intensive and extensive researches, the present inventors have found apo A-I-binding activity in the CUB7–CUB14 fragment peptide (Blood 91, 3593–3600 (1998)) and the CUB9–CUB14 fragment peptide of cubilin. Then, the inventors have developed an experimental system for measuring apo A-I-binding using these fragments. Based on these findings, the inventors have made further investigations. Thus, the present invention has been achieved.

The present invention relates to:

(1) A polypeptide having the ability to bind to apolipoprotein A-I, which is a partial fragment of cubilin, an amide or ester of said polypeptide, or a salt of said polypeptide, (2) The polypeptide, amide or ester thereof, or salt thereof of (1) above, wherein the polypeptide is characterized by having an amino acid sequence identical or substantially identical with the amino acid sequence as shown in SEQ ID NO: 10, (3) The polypeptide, amide or ester thereof, or salt thereof of (1) above, wherein the polypeptide has the amino acid sequence as shown in SEQ ID NO: 10, (4) The polypeptide, amide or ester thereof, or salt thereof of (1) above, wherein the polypeptide is characterized by having an amino acid sequence identical or substantially identical with the amino acid sequence as shown in SEQ ID NO: 19, (5) The polypeptide, amide or ester thereof, or salt thereof of (1) above, wherein the polypeptide has the amino acid sequence as shown in SEQ ID NO: 19, (6) A DNA comprising a DNA encoding the polypeptide of (1) above, (7) The DNA of (6) above, wherein the DNA comprises the base sequence as shown in SEQ ID NO: 9, (8) The DNA of (6) above, wherein the DNA comprises the base sequence as shown in SEQ ID NO: 22, (9) A recombinant vector comprising the DNA of (6) above,

(10) A transformant transformed with the recombinant vector of (9) above,

(11) A method of producing the polypeptide, amide or ester thereof, or salt thereof of (1) above, which is characterized by culturing the transformant of (10) above and allowing the transformant to produce the polypeptide,

(12) An antibody to the polypeptide, amide or ester thereof, or salt thereof of (1) above,

(13) A method of screening for compounds or salts thereof that promote or inhibit the activity of the polypeptide or salt thereof of (1) above, wherein the method is characterized by using the polypeptide, amide or ester thereof, or salt thereof of (1) above,

(14) A screening kit for compounds or salts thereof that promote or inhibit the activity of the polypeptide, amide or ester thereof, or salt thereof of (1) above, wherein the kit comprises the polypeptide or salt thereof of (1) above,

(15) A compound or salt thereof that promotes or inhibits the activity of the polypeptide, amide or ester thereof, or salt thereof of (1) above, wherein said compound or salt thereof is obtainable by using the screening method of (13) above or the screening kit of (14) above,

(16) A medicine comprising a compound or salt thereof that promotes or inhibits the activity of the polypeptide, amide or ester thereof, or salt thereof of (1) above, wherein said compound or salt thereof is obtainable by using the screening method of (13) above or the screening kit of (14) above,

(17) A prophylactic and/or therapeutic agent for renal disorders, nephritis, nephropathy, proteinuria, nervous disorders or vitamin $B_{12}$ deficiency, comprising a compound or salt thereof that promotes or inhibits the activity of the polypeptide, amide or ester thereof, or salt thereof of (1) above, wherein said compound or salt thereof is obtainable by using the screening method of (13) above or the screening kit of (14) above,

(18) A prophylactic and/or therapeutic agent for hyperlipemia, hypertriglyceridemia, hypo-high density lipoproteinemia, hypoapolipoproteinemia A-I, after meal hyperlipemia, diabetes, obesity, arteriosclerosis, myocardial infarction or angina, comprising a compound or salt thereof that promotes or inhibits the activity of the polypeptide, amide or ester thereof, or salt thereof of (1) above, wherein said compound or salt thereof is obtainable by using the screening method of (13) above or the screening kit of (14) above,

(19) A medicine comprising the polypeptide, amide or ester thereof, or salt thereof of (1) above,

(20) A prophylactic and/or therapeutic agent for diabetes, obesity, arteriosclerosis, hyperlipemia, hypertriglyceridemia, hypo-high density lipoproteinemia, hypoapolipoproteinemia A-I or nervous disorders, comprising the polypeptide, amide or ester thereof, or salt thereof of (1) above,

(21) A diagnostic agent that is characterized by the use of the DNA of (6) above

(22) A diagnostic agent comprising the antibody of (12) above,.

(23) A method for preventing and/or treating renal disorders, nephritis, nephropathy, proteinuria, nervous disorders or vitamin $B_{12}$ deficiency in a mammal, comprising a compound or salt thereof that promotes or inhibits the activity of the polypeptide, amide or ester thereof, or salt thereof of (1) above, wherein said compound or salt thereof is obtainable by using the screening method of (13) above or the screening kit of (14) above,

(24) A method for preventing and/or treating hyperlipemia, hypertriglyceridemia, hypo-high density lipoproteinemia, hypoapolipoproteinemia A-I, after meal hyperlipemia, diabetes, obesity, arteriosclerosis, myocardial infarction or angina, characterized by administering to a mammal an effective amount of a compound or salt thereof that promotes or inhibits the activity of the polypeptide, amide or ester thereof, or salt thereof of (1) above, wherein said compound or salt thereof is obtainable by using the screening method of (13) above or the screening kit of (14) above,

(25) Use of a compound or salt thereof that promotes or inhibits the activity of the polypeptide, amide or ester thereof, or salt thereof of (1) above, for manufacturing a prophylactic and/or therapeutic agent for hyperlipemia, hypertriglyceridemia, hypo-high density lipoproteinemia, hypoapolipoproteinemia A-I, after meal hyperlipemia, diabetes, obesity, arteriosclerosis, myocardial infarction or angina, wherein said compound or salt thereof is obtainable by using the screening method of (13) above or the screening kit of (14) above,

(26) A method for preventing and/or treating diabetes, obesity, arteriosclerosis, hyperlipemia, hypertriglyceridemia, hypo-high density lipoproteinemia, hypoapolipoproteinemia A-I or nervous disorders, characterized by administering to a mammal an effective amount of the polypeptide, amide or ester thereof, or salt thereof of (1) above, and

(27) Use of the polypeptide, amide or ester thereof, or salt thereof of (1) above for manufacturing a prophylactic and/or therapeutic agent for diabetes, obesity, arteriosclerosis, hyperlipemia, hypertriglyceridemia, hypo-high density lipoproteinemia, hypoapolipoproteinemia A-I or nervous disorders.

Further, the present invention provides:

(28) The polypeptide, amide or ester thereof, or salt thereof of (2) or (4) above, wherein the amino acid sequence substantially identical with the amino acid sequence as shown in SEQ ID NO: 10 or SEQ ID NO: 19 is an amino acid sequence having about 50% or more (preferably about 60% or more, more preferably about 70% or more, still more preferably about 80% or more, especially preferably about 90% or more, and most preferably about 95% or more) homology to the amino acid sequence as shown in SEQ ID NO: 10 or SEQ ID NO: 19, and

(29) The polypeptide, amide or ester thereof, or salt thereof of (2) or (4) above, wherein the amino acid sequence substantially identical with the amino acid sequence as shown in SEQ ID NO: 10 or SEQ ID NO: 19 is (i) an amino acid sequence wherein one or more amino acids (preferably about 1–30 amino acids) are deleted from the amino acid sequence as shown in SEQ ID NO: 10 or SEQ ID NO: 19; (ii) an amino acid sequence wherein one or more amino acids (preferably about 1–30 amino acids) are added to the amino acid sequence as shown in SEQ ID NO: 10 or SEQ ID NO: 19; (iii) an amino acid sequence wherein one or more amino acids (preferably about 1–30 amino acids) amino acids are substituted with other amino acids in the amino acid sequence as shown in SEQ ID NO: 10 or SEQ ID NO: 19; or (iv) an amino acid sequence which is a combination of these sequences.

Further, the DNA of the invention and the polypeptide, amide or ester thereof, or salt thereof of the invention may be utilized in basic researches such as molecular markers, tissue markers, chromosome mapping, identification of genetic diseases or designing of primers, probes, and so on.

BRIEF DESCRIPTION OF THE DRAWINGS

FIG. 1 shows the amino acid sequence of a human cubilin mature protein (to be continued to FIG. 2).

FIG. 2 shows the amino acid sequence of a human cubilin mature protein (continued from FIG. 1).

The utmost left lane in each blotting shows the migration of molecular markers.

Mock, Cub7–12, Cub9–14, Cub7–14 and Cub13–20 represent vectors transfected into COS7 cells. Mock means a vector alone. Cub7–12 means a vector expressing a cDNA encoding the CUB7–CUB12 fragment peptide, and Cub9–14 means a vector expressing a cDNA encoding the CUB9–CUB14 fragment peptide. Cub7–14 corresponds to the fragment III described in Example 3, and Cub13–20 corresponds to the fragment IV described in Example 3.

In this Figure, "Sample" denotes sample solutions applied to human apolipoprotein A-I-binding resin; "Column" denotes fractions passed through columns; "Wash" denotes fractions eluted at the time of washing; and "Elution" denotes fractions eluted by EDTA. In the "Pass" panel, the bands appearing at approx. 70 kDa are considered to be non-specific recognition bands attributable to high concentration albumin.

Figure 6:
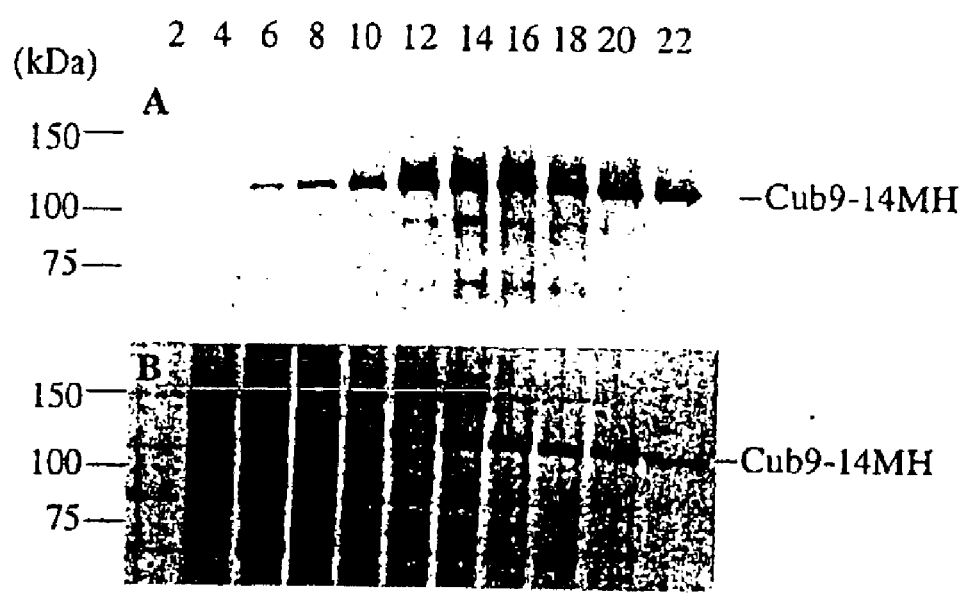

FIG. 6 shows the results of Western blotting (A) and CBB staining (B) carried out in Example 6. The numbers of individual lanes correspond to the Nos. of fractions eluted with 10 mM–200 mM imidazole gradient in Example 6.

Figure 7:
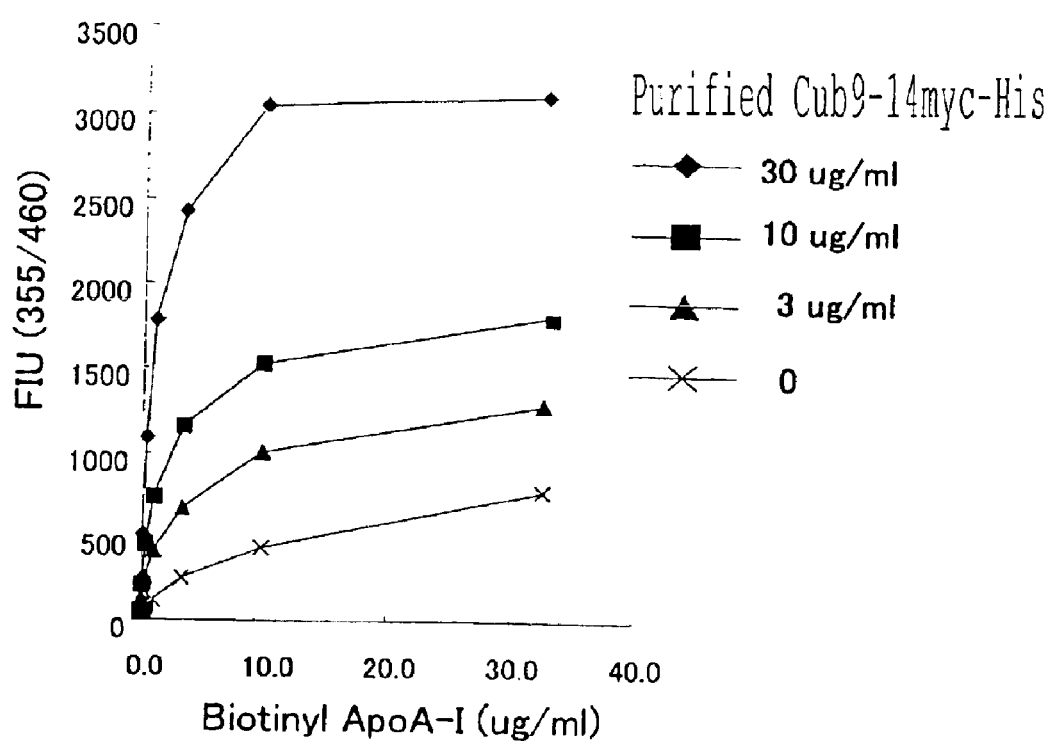

FIG. 7 shows the biotin-added human apolipoprotein A-I-binding curve obtained in Example 7. In this Figure, "FIU" denotes values quantitatively determined with a fluorescence measuring apparatus.

BEST MODE FOR CARRYING OUT THE INVENTION

The polypeptide of the invention that is a partial fragment of cubilin having the ability to bind to apolipoprotein A-I (hereinafter, sometimes simply referred to as the "polypeptide of the invention") may be a polypeptide derived from cells of human or other warm-blooded animals (e.g. guinea pig, rat, mouse, chicken, rabbit, pig, sheep, bovine, or monkey), such as hepatocyte, splenocyte, nerve cell, glia cell, pancreatic β cell, bone marrow cell, mesangial cell, Langerhans' cell, epidermic cell, epithelial cell, endothelial cell, fibroblast, fibrocyte, myocyte, fat cell, immune cell (e.g. macrophage, T cell, B cell, natural killer cell, mast cell, neutrophil, basophil, eosinophil, monocyte), megakaryocyte, synovial cell, cartilage cell, bone cell, osteoblast, osteoclast, mammary gland cell or interstitial cell; or precursor cells, stem cells or cancer cells of these cells; or may be a polypeptide derived from any of the tissues where such cells are present, such as brain, any region thereof (e.g. olfactory bulb, amygdaloid nucleus, basal ganglia, hippocampus, thalamus, hypothalamus, cerebral cortex, medulla, or cerebellum), spinal cord, pituitary, stomach, pancreas, kidney, liver, gonad, thyroid, gallbladder, bone marrow, adrenal gland, skin, muscle, lung, gastrointestinal tract (e.g. large intestine and small intestine), blood vessel, heart, thymus, spleen, salivary gland, peripheral blood, prostate, testis, ovary, placenta, uterus, bone, cartilage, joint, skeletal muscle, etc. Alternatively, the polypeptide of the invention may be a recombinant polypeptide or a synthetic polypeptide.

When the polypeptide of the invention has a signal peptide, the polypeptide may be efficiently secreted out of cells.

The partial fragment of cubilin having the ability to bind to apolipoprotein A-I may be any partial peptide as long as it is a partial peptide of cubilin and has the ability to bind to apolipoprotein A-I. Preferably, the partial peptide is a polypeptide having an amino acid sequence identical or substantially identical with the amino acid sequence as shown in SEQ ID NO: 10 or a polypeptide having an amino acid sequence identical or substantially identical with the amino acid sequence as shown in SEQ ID NO: 19.

As an amino acid sequence substantially identical with the amino acid sequence as shown in SEQ ID NO: 10, an amino acid sequence having about 50% or more, preferably about 60% or more, more preferably about 70% or more, still more preferably about 80% or more, especially preferably about 90% or more, and most preferably about 95% or more homology to the amino acid sequence as shown in SEQ ID NO: 10 may be given.

As an amino acid sequence substantially identical with the amino acid sequence as shown in SEQ ID NO: 19, an amino acid sequence having about 50% or more, preferably about 60% or more, more preferably about 70% or more, still more preferably about 80% or more, especially preferably about 90% or more, and most preferably about 95% or more homology to the amino acid sequence as shown in SEQ ID NO: 19 may be given.

As a polypeptide having an amino acid sequence substantially identical with the amino acid sequence as shown in SEQ ID NO: 10, such a polypeptide is preferable that has the above-described amino acid sequence substantially identical with the amino acid sequence as shown in SEQ ID NO: 10 and yet has a substantially identical nature with a nature of a polypeptide having the amino acid sequence as shown in SEQ ID NO: 10.

As a polypeptide having an amino acid sequence substantially identical with the amino acid sequence as shown in SEQ ID NO: 19, such a polypeptide is preferable that has the above-described amino acid sequence substantially identical with the amino acid sequence as shown in SEQ ID NO: 19 and yet has a substantially identical nature with a nature of a polypeptide having the amino acid sequence as shown in SEQ ID NO: 19.

As a substantially identical nature, a nature to bind to apolipoprotein A-I may be given, for example. The term "substantially identical" means that such a nature is qualitatively identical. Therefore, it is preferable that a nature such as apolipoprotein A-I-binding ability is identical (e.g. about 0.1- to about 100-fold, preferably about 0.5- to about 10-fold, more preferably about 0.5- to about 2-fold), but quantitative factors such as the extent of that nature, the molecular weight of the polypeptide, etc. may be different.

More specifically, examples of the polypeptide comprising an amino acid sequence substantially identical with the amino acid sequence as shown in SEQ ID NO: 10 or SEQ ID NO: 19 include polypeptides (the so-called muteins) comprising (i) an amino acid sequence wherein one or more amino acids (preferably about 1–30, more preferably about 1–10, still more preferably several (1–5) amino acids) are deleted from the amino acid sequence as shown in SEQ ID NO: 10 or SEQ ID NO: 19; (ii) an amino acid sequence wherein one or more amino acids (preferably about 1–30, more preferably about 1–10, still more preferably several (1–5) amino acids) are added to the amino acid sequence as shown in SEQ ID NO: 10 or SEQ ID NO: 19; (iii) an amino acid sequence wherein one or more amino acids (preferably about 1–30, more preferably about 1–10, still more preferably several (1–5) amino acids) are inserted into the amino acid sequence as shown in SEQ ID NO: 10 or SEQ ID NO: 19; (iv) an amino acid sequence wherein one or more amino acids (preferably about 1–30, more preferably about 1–10, still more preferably several (1–5) amino acids) amino acids are substituted with other amino acids in the amino acid sequence as shown in SEQ ID NO: 10 or SEQ ID NO: 19; or (v) an amino acid sequence which is a combination of these sequences.

When the amino acid sequence has insertion(s), deletion(s) or substitution(s) as described above, the positions of such insertion(s), deletion(s) or substitution(s) are not particularly limited. However, such positions are preferably those which are not essential for the apo A-I-binding in the amino acid sequence of SEQ ID NO: 10 or SEQ ID NO: 19.

Throughout this specification, the left end of each polypeptide is its N-terminus, and the right end thereof is its C-terminus according to the convention in peptide description. The C-terminus of the polypeptide of the invention (such as a polypeptide comprising the amino acid sequence as shown in SEQ ID NO: 10) is usually a carboxyl group (—COOH) or a carboxylate (—COO⁻), but it may be an amide (—CONH$_2$) or an ester (—COOR).

Examples of R of the above ester group include $C_{1-6}$ alkyl groups (e.g. methyl, ethyl, n-propyl, isopropyl or n-butyl), $C_{3-8}$ cycloalkyl groups (e.g. cyclopentyl or cyclohexyl), $C_{6-12}$ aryl groups (e.g. phenyl or α-naphthyl), $C_{7-14}$ aralkyl groups such as phenyl-$C_{1-2}$ alkyl groups (e.g. benzyl or phenethyl) and α-naphthyl-$C_{1-2}$ alkyl groups (e.g. α-naphthylmethyl). In addition, the ester group also includes pivaloyloxymethyl esters that are universally used as oral esters.

When the polypeptide of the invention has a carboxyl group (or carboxylate) at any position other than its C-terminus, such a polypeptide that the carboxyl group may be amidated or esterified is also included in the polypeptide of the invention. The ester in this case may be, for example, any of the esters mentioned above for the C-terminal ester.

Furthermore, the polypeptide of the present invention includes those polypeptides in which the N-terminal amino acid residue (e.g. Met) is protected by a protective group (e.g. $C_{1-6}$ acyl group such as $C_{1-6}$ alkanoyl group (e.g. formyl group or acetyl group)); those polypeptides in which the N-terminal Glu generated through in vivo cleavage is pyroglutaminated; those polypeptides in which a substituent on a side chain of an amino acid (e.g. OH, SH, amino group, imidazole group, indole group, or guannidino group) is protected by an appropriate protective group (e.g. $C_{1-6}$ acyl group such as $C_{1-6}$ alkanoyl group (e.g. formyl group or acetyl group)); and conjugated polypeptides such as the so-called glycopolypeptides to which sugar chains are linked.

As the salt of the polypeptide of the invention, salts formed with physiologically acceptable acids (e.g. organic or inorganic acids) or bases (e.g. alkali metals) are used. Especially preferable are physiologically acceptable acid addition salts. Examples of such salts include salts formed with inorganic acids (e.g. hydrochloric acid, phosphoric acid, hydrobromic acid or sulfuric acid) and salts formed with organic acids (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid).

The polypeptide or salt thereof of the present invention can be produced from the afore-mentioned cells or tissues of human or other warm-blooded animals by publicly known purification methods for polypeptides (proteins). Alternatively, the polypeptide of the invention can be produced by culturing a transformant described later comprising a DNA encoding the polypeptide. It can also be produced in accordance with the procedures for peptide synthesis which are described later.

When the polypeptide of the invention is produced from tissues or cells of human or other warm-blooded animals, the relevant tissue or cell is homogenized and then the polypeptide of the present invention is extracted with acids, etc. The polypeptide can be purified and isolated from the resultant extract by a combination of chromatography, such as reversed phase chromatography, ion exchange chromatography and so on.

For the synthesis of the polypeptide of the invention or salt or amide thereof, any of the commercially available resins for polypeptide synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenylacetamidomethyl resin, polyacrylamide resin, 4-(2',4'-dimethoxyphenylhydroxymethyl)phenoxy resin, and 4-(2',4'-dimethoxyphenyl-Fmoc-aminoethyl)phenoxy resin. Using such a resin, amino acids appropriately protected at their α-amino groups and side chain functional groups are condensed on the resin according to the amino acid sequence of the polypeptide of interest by publicly known condensation methods. At the final stage of the reaction, all protective groups are removed simultaneously with the cleavage of the polypeptide from the resin. Then, in a highly diluted solution, intramolecular disulfide bond formation reaction is carried out to obtain the polypeptide of interest or amide thereof.

With respect to the above-described condensation of protected amino acids, various activators useful for polypeptide synthesis may be utilized. Among all, carbodiimide reagents are especially preferred. Examples of carbodiimide reagents include DCC, N,N'-diisopropylcarbodiimide, and N-ethyl-N'-(3-dimethylaminoprolyl)carbodiimide. For activation by these reagents, protected amino acids and a recemization inhibitor (e.g. HOBt or HOOBt) may be directly added to the resin, or protected amino acids may be activated in advance in the form of symmetric acid anhydride, HOBt ester or HOOBt ester and, then, added to the resin.

The solvent used for the above-mentioned activation of protected amino acids or the condensation thereof with a resin may be appropriately selected from those solvents known to be useful for polypeptide (protein) condensation reactions. Examples of useful solvents include acid amides (e.g. N,N-dimethylformamide, N,N-dimethylacetamide, of N-methylpyrrolidone), halogenated hydrocarbons (e.g. methylene chloride, or chloroform), alcohols (e.g. trifluoroethanol), sulfoxides (e.g. dimethyl sulfoxide), ethers (e.g. pyridine, dioxane, tetrahydrofuran), nitriles (e.g. acetonitrile or propionitrile), esters (e.g. methyl acetate or ethyl acetate), and suitable mixtures of these solvents. The reaction temperature may be appropriately selected from the range known to be useful for polypeptide-forming reactions; usually, the temperature is selected from the range from about −20° C. to about 50° C. The activated amino acid derivative is usually used in 1.5- to 4-fold excess. When the condensation is found insufficient as a result of test using the ninhydrin reaction, sufficient condensation can be achieved by repeating reactions without removing protective groups. When sufficient condensation cannot be achieved even by repeating reactions, unreacted amino acids may be acetylated with acetic anhydride or acetylimidazole so that they do not affect subsequent reactions.

Examples of useful protective groups for the amino group of raw materials include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulfenyl, diphenylphosphinothioyl, and Fmoc.

The carboxyl group can be protected, for example, in the form of an alkyl ester (e.g. straight-chain, branched, or cyclic alkyl esters such as methyl, ethyl, propyl, butyl, t-butyl, cyclopentyl, cyclohexyl, cycloheptyl, cyclooctyl, 2-adamantyl, and so on), aralkyl ester (e.g. benzyl, 4-nitrobenzyl, 4-methoxybenzyl, 4-chlorobenzyl, benzhydryl, and so on), phenacyl ester, benzyloxycarbonylhydrazide, t-butoxycarbonylhydrazide or tritylhydrazide.

The hydroxyl group of serine can be protected, for example, by esterification or etherification. Examples of suitable groups for this esterification include lower ($C_{1-6}$) alkanoyl groups such as acetyl, aroyl groups such as benzoyl, and carbonic acid-derived groups such as benzyloxycarbonyl and ethyloxycarbonyl. Examples of groups suitable for the etherification include benzyl, tetrahydropyranyl and t-butyl.

Examples of protective groups for the phenolic hydroxyl group of tyrosine include Bzl, $Cl_2$-Bzl, 2-nitrobenzyl, BrZ, and t-butyl.

Examples of protective groups for the imidazole ring of histidine include Tos, 4-methoxy-2,3,6-trimethylbenzenesulfonyl, DNP, benzyloxymethyl, Bum, Boc, Trt and Fmoc.

Examples of raw materials with activated carboxyl groups include the corresponding acid anhydrides, azides and active esters (esters of alcohols such as pentachlorophenol, 2,4,5-trichlorophenol, 2,4-dinitrophenol, cyanomethyl alcohol, p-nitrophenol, HONB, N-hydroxysuccinimide, N-hydroxyphthalimide and HOBt). Examples of raw materials with activated amino groups include the corresponding phosphoric acid amides.

Methods for removing (eliminating) protective groups include, for example, catalytic reduction in a hydrogen stream in the presence of a catalyst such as Pd black or Pd-carbon, acid treatment with anhydrous hydrogen fluoride, methanesulfonic acid, trifluoromethanesulfonic acid, trifluoroacetic acid or mixtures thereof, base treatment with diisopropylethylamine, triethylamine, piperidine, piperazine, or the like, and reduction with sodium in liquid ammonia The elimination reaction by the above-mentioned acid treatment is generally conducted at temperatures of about −20° C. to about 40° C. In the acid treatment, it is effective to add a cation scavenger such as anisole, phenol, thioanisole, m-cresol, p-cresol, dimethylsulfide, 1,4-butanedithiol or 1,2-ethanedithiol. The 2,4-dinitrophenyl group used as the protective group for the imidazole of histidine is removed by thiophenol treatment. The formyl group used as the protective group for the indole of tryptophan may be removed by the above-mentioned deprotection by the acid treatment in the presence of 1,2-ethanedithiol, 1,4-butanedithiol or the like, or by alkali treatment using dilute sodium hydroxide, dilute ammonia or the like.

The protection of functional groups in raw materials that should not be involved in the reaction, protective groups therefor, the removal of these protective groups and the activation of functional groups involved in the reaction can be appropriately selected from groups or methods publicly known.

An alternative method for obtaining amides of a polypeptide of interest comprises, for example, protecting the α-carboxyl group of the C-terminal amino acid by amidation, extending the peptide (polypeptide) chain to a desired length on the side of the amino group, preparing a polypeptide with its N-terminal α-amino group selectively deprotected, preparing a polypeptide with its C-terminal carboxyl group selectively deprotected, and condensing these two polypeptides in a mixed solvent such as described above. Details of this condensation reaction are the same as described above. After purification of the protected polypeptide thus obtained by condensation, all the protective groups are removed by the method described above to thereby provide a crude polypeptide of interest. This crude polypeptide is purified by various known purification techniques and the major fractions are lyophilized to provide the desired polypeptide in an amide form.

A method for obtaining esters of a polypeptide of interest comprises, for example, condensing the α-carboxyl group of the C-terminal amino acid with a desired alcohol to prepare the corresponding amino acid ester, and subjecting this ester to the same procedures as described above in the preparation of amides to thereby provide the desired polypeptide in an ester form.

The polypeptide of the invention or salt thereof can be produced by publicly known methods for peptide synthesis. The method for peptide synthesis may be solid-phase synthesis or liquid-phase synthesis. Briefly, a peptide of interest can be produced by condensing a partial peptide or amino acid capable of constituting the partial peptide of the invention with the residual part thereof and, if the product has protective groups, removing the protective groups. Examples of condensation methods and methods for removal of protective groups publicly known include those described in the following references (1) to (5).

(1) M. Bodanszky & M. A. Ondetti, Peptide Synthesis, Interscience Publishers, New York, 1966
(2) Schroeder & Luebke, The Peptide, Academic Press, New York, 1965
(3) Nobuo Izumiya et al., Fundamentals and Experiments in Peptide Synthesis, Maruzen, 1975
(4) Haruaki Yajima and Shumpei Sakakibara, Biochemical Experiment Series 1, Polypeptide Chemistry IV, 205, 1977
(5) Haruaki Yajima (ed.), Development of Drugs (Continued), Vol. 14, Peptide Synthesis, Hirokawa Shoten After the reaction, the polypeptide of the invention can be isolated and purified by a combination of conventional purification techniques such as solvent extraction, distillation, column chromatography, liquid chromatography, and recrystallization. When the polypeptide thus obtained is a free form, it can be converted to a suitable salt by publicly known methods or methods based thereon. On the contrary, when the polypeptide is obtained in a salt form, it can be converted to a free form or another salt by publicly known methods or methods based thereon.

The DNA encoding the polypeptide of the invention may be any DNA as long as it comprises a base sequence encoding the above-described polypeptide of the invention. The DNA may be genomic DNA, cDNA derived from the above-mentioned cells or tissues, or synthetic DNA.

Vectors used for library may be any vectors such as bacteriophage, plasmid, cosmid, phagemid, and so on. Alternatively, total RNA or mRNA fraction may be prepared from the above-mentioned cells or tissues, followed by direct amplification by reverse transcriptase polymerase chain reaction (hereinafter, referred to as "RT-PCR").

Examples of DNA encoding the polypeptide of the invention include a DNA comprising the base sequence as shown in SEQ ID NO: 9 or SEQ ID NO: 22; or a DNA which has a base sequence hybridizing to the base sequence as shown in SEQ ID NO: 9 or SEQ ID NO: 22 under high stringent conditions and encodes a polypeptide having a property (e.g. immunogenicity) substantially identical with the corresponding property of the polypeptide of the invention. Any of such DNA may be used.

As a DNA hybridizable to the base sequence as shown in SEQ ID NO: 9 under high stringent conditions, a DNA comprising a base sequence having about 60% or more, preferably about 70% or more, and more preferably about 80% or more homology to the base sequence as shown in SEQ ID NO: 9 may be used, for example.

As a DNA hybridizable to the base sequence as shown in SEQ ID NO: 22 under high stringent conditions, a DNA comprising a base sequence having about 60% or more, preferably about 70% or more, and more preferably about 80% or more homology to the base sequence as shown in SEQ ID NO: 22 may be used, for example.

Hybridization can be carried out according to publicly known methods or methods based thereon, e.g. those methods described in Molecular Cloning, 2nd Ed. (J. Sambrook et al., Cold Spring Harbor Lab. Press, 1989) and the like. When commercial libraries are used, hybridization can be carried out in accordance with the methods described in the instructions attached to the kits; preferably, hybridization is carried out under high stringent conditions.

"High stringent conditions" refers to, for example, conditions where sodium concentration is about 19–40 mM, preferably about 19–20 mM, and temperature is about 50–70° C., preferably about 60–65° C.

As a DNA encoding the polypeptide of the invention having the amino acid sequence as shown in SEQ ID NO: 10, a DNA having the base sequence as shown in SEQ ID NO: 9 may be used, for example. As a DNA encoding the polypeptide of the invention having the amino acid sequence as shown in SEQ ID NO: 19, a DNA having the base sequence as shown in SEQ ID NO: 22 may be used, for example.

A DNA encoding the entire polypeptide of the invention can be cloned either by PCR amplification using synthetic DNA primers each having a partial base sequence encoding the polypeptide of the invention, or by hybridization of DNA fragments inserted into a suitable vector to a labeled DNA fragment encoding a part or full length of the polypeptide of the invention or a labeled synthetic DNA fragment. The hybridization can be carried out, for example, according to the method described in Molecular Cloning, 2nd Edition (J. Sambrook et al., Cold Spring Harbor Lab. Press, 1989). When commercial libraries are used, the hybridization can be carried out according to the instructions attached thereto.

Substitution of the base sequence of a DNA can be performed by publicly known methods such as ODA-LA PCR, gapped duplex method, Kunkel method and the like using publicly known kits such as Mutan™-Super Express Km (Takara), Mutan™-K (Takara), etc.

The cloned DNA encoding the polypeptide of the invention may be used as it is or after digestion with restriction enzymes or addition of linkers, if desired. The DNA may have ATG at its 5' end as the translation initiation codon and TAA, TGA, or TAG at its 3' end as the translation termination codon. The translation initiation and termination codons may be added by using appropriate synthetic DNA adapters.

Expression vectors for the polypeptide of the invention can be prepared by, for example, (a) cutting out a DNA fragment of interest from a DNA encoding the polypeptide of the invention and (b) ligating the DNA fragment to an appropriate expression vector downstream of its promoter.

Examples of vectors include plasmids derived from *Escherichia coli* (e.g. pBR322, pBR325, pUC12, and pUC13); plasmids derived from *Bacillus subtilis* (e.g. pUB110, pTP5 and pC194); plasmids derived from yeast (e.g. pSH19 and pSH15); bacteriophages such as λ-phage; animal viruses such as retrovirus, vaccinia virus, baculovirus; and other vectors such as pA1–11, pXT1, pRc/CMV, pRc/RSV, pcDNAI/Neo and so on.

Any promoter may be used in the invention as long as it is appropriate for the host that will be used for expressing a gene of interest. When the host is an animal cell, examples of promoters include SRα promoter, SV40 promoter, LTR promoter, CMV promoter, HSV-TK promoter and β-actin promoter.

Among these promoters, CMV (cytomegalovirus) promoter, SRα promoter or the like is preferably used. When the host is *Escherichia*, trp promoter, lac promoter, recA promoter, λP$_L$ promoter, lpp promoter, T7 promoter or the like is preferably used. When the host is Bacillus, SPO1 promoter, SPO2 promoter, penP promoter or the like is preferably used. When the host is a yeast, PHO5 promoter, PGK promoter, GAP promoter, ADH promoter, or the like is preferably used. When the host is an insect cell, polyhedrin promoter, P10 promoter, or the like is preferably used.

The expression vectors may, if desired, further comprise enhancers, splicing signals, polyadenylation signals, selective markers, SV40 replication origin (hereinafter, sometimes abbreviated to "SV40 ori") and the like. Examples of selective markers include dihydrofolate reductase (hereinafter, sometimes abbreviated to "dhfr") gene [methotorexate (MTX) resistance], ampicillin resistance gene (hereinafter, sometimes abbreviated to "Amp$^r$"), neomycin resistance gene (hereinafter, sometimes abbreviated to "Neo$^r$": Geneticin resistance) and the like. When dhfr gene-deficient Chinese hamster cells are used in combination with dhfr gene as a selective marker, recombinant cells may be selected even in a thymidine-free medium.

Furthermore, a signal sequence appropriate for the host may be added, if necessary, to the N-terminal of the polypeptide. When the host is *Escherichia*, the utilizable signal sequences may include PhoA signal sequence, OmpA signal sequence, or the like may be added. When the host is *Bacillus*, α-amylase signal sequence, subtilisin signal sequence, or the like may be added. When the host is yeast, MFα signal sequence, SUC2 signal sequence, or the like may be added. When the host is an animal cell, insulin signal sequence, α-interferon signal sequence, antibody molecule signal sequence, or the like may be added.

When the polypeptide of the invention has such a signal sequence as described above, the polypeptide of the invention is secreted out of cells effectively.

Transformants (or transfectants) can be prepared by using the thus constructed vector comprising a DNA encoding the polypeptide of the invention.

Examples of hosts include bacteria belonging to the genus *Escherichia*, bacteria belonging to the genus *Bacillus*, yeasts, insect cells, insects, and animal cells.

Specific examples of bacteria belonging to the genus *Escherichia* include *E coli* K12 DH1 (Proc. Natl. Acad. Sci. USA, Vol. 60, 160 (1968)), JM103 (Nucleic Acids Research, Vol. 9, 309 (1981)), JA221 (Journal of Molecular Biology, Vol. 120, 517 (1978)), HB101 (Journal of molecular Biology, Vol, 41, 459 (1969)) and C600 (Genetics, Vol. 39, 440 (1954)).

Specific examples of bacteria belonging to the genus *Bacillus* include *B. subtilis* MI114 (Gene, Vol. 24, 255 (1983)) and 207–21 (Journal of Biochemistry, Vol. 95, 76 (1984)).

Specific examples of yeasts include *Saccharomyces cerevisiae* AH22, AH22R$^-$, NA87-11A, DKD-5D and 20B-12, *Schizosaccharomyces pombe* NCYC1913 and NCYC2036, and *Pichia pastoris* KM71.

Specific examples of insect cells include, when the virus used is AcNPV, a cell line derived from larvae of *Spodoptera frugiperda* (Sf cells), MG1 cells derived from the midgut of *Trichoplusia ni,* High Five™ cells derived from eggs of *Trichoplusia ni, Mamestra brassicae*-derived cells and *Estigmena acrea*-derived cells. When the virus used is BmNPV, insect cells such as a silkworm-derived cell line (*Bombyx mori* N cells; BmN cells) may be used. Specific examples of Sf cells useful in the invention include Sf9 cells (ATCC CRL 1711) and Sf21 cells (both disclosed in Vaughn J. L. et al., In Vivo, 13, 213–217 (1977)).

Specific examples of insects include larvae of silkworm (Maeda et al., Nature, 315, 592 (1985)).

Specific examples of animal cells include a simian cell COS-7 (COS7), Vero cells, a Chinese hamster cell CHO (CHO cells), a dhfr gene-deficient Chinese hamster cell CHO (hereinafter, abbreviated to "CHO(dhfr$^-$) cells"), mouse L cells, mouse AtT-20 cells, mouse myeloma cells, rat GH3 cells, and human FL cells.

Transformation of bacteria belonging to the genus *Escherichia* can be performed in accordance with methods disclosed, for example, in Proc. Natl. Acad. Sci. USA, Vol. 69, 2110 (1972) and Gene, Vol. 17, 107 (1982).

Transformation of bacteria belonging to the genus *Bacillus* can be performed in accordance with methods disclosed, for example, in Molecular & General Genetics, Vol. 168, 111 (1979).

Transformation of yeasts can be performed in accordance with methods disclosed, for example, in Methods in Enzymology, 194, 182–187 (1991) and Proc. Natl. Acad. Sci. USA, Vo. 75, 1929 (1978).

Transformation of insect cells or insects can be performed in accordance with methods disclosed, for example, in Bio/Technology, 6, 47–55 (1988).

Transformation of animal cells can be performed by methods disclosed, for example, in Cell Engineering, Separate Vol. 8, New Cell Engineering Experiment Protocol, 263–267 (1995) (Shujunsha Co.) and Virology, Vol. 52, 456 (1973).

Thus, transformants transformed with an expression vector comprising a DNA encoding the polypeptide of the invention can be obtained.

As a medium to culture transformants obtained from *Escherichia* or *Bacillus* bacteria as hosts, a liquid medium is appropriate. The medium is allowed to contain carbon sources, nitrogen sources, minerals, and so on which are necessary for the growth of the transformant. As carbon sources, glucose, dextrin, soluble starch, sucrose or the like may be enumerated. As nitrogen sources, organic or inorganic substances such as ammonium salts, nitrates, corn steep liquor, peptone, casein, yeast extract, meat extract, bean cake, potato extract, or the like may be enumerated. As minerals, calcium chloride, sodium dihydrogen phosphate, magnesium chloride, or the like may be enumerated. Further, yeast extract, vitamins, growth-promoting factors, etc. may also be added to the medium. Preferable pH of the medium is about 5 to about 8.

As a medium to culture *Escherichia* bacteria, M9 medium containing glucose and casamino acid (Miller, Journal of Experiments in Molecular Genetics, 431–433, Cold Spring Harbor Laboratory, New York, (1972)) is preferable, for example. If necessary, drugs such as 3β-indolyl acrylic acid can be added to the medium to improve efficiency of the promoter.

When the host is an *Escherichia* bacterium, the transformant is cultured usually at about 15–43° C. for about 3–24 hours. If necessary, aeration and stirring may be applied.

When the host is a *Bacillus* bacterium, the transformant is cultured usually at about 30–40° C. for about 6–24 hours. If necessary, aeration and stirring may also be applied.

As a medium to culture transformants obtained from yeasts as hosts, a medium such as Burkholder minimum medium (Bostian, K. L. et al., Proc. Natl. Acad. Sci. USA, Vol. 77, 4505 (1980)) or SD medium containing 0.5% casamino acid (Bitter, G. A. et al., Proc. Natl. Acad. Sci. USA, Vol. 81, 5330 (1984)) may be used, for example. It is preferable that the pH of the medium is adjusted to about 5 to about 8. The transformant is cultured usually at about 20–35° C. for about 24–72 hours. If necessary, aeration and stirring may be applied.

As a medium to culture transformants obtained from insect cells or insects as hosts, Grace's Insect Medium (Grace, T. C. C., Nature, 195, 788 (1962)) supplemented with additives such as inactivated 10% bovine serum may be used, for example. It is preferable that the pH of the medium is adjusted to about 6.2–6.4. The transformant is cultured usually at about 27° C. for about 3–5 days. If necessary, aeration and stirring may be applied.

As a medium to culture transformants obtained from animal cells as hosts, examples of useful media include MEM medium (Science, Vol. 122, 501 (1952)) containing about 5–20% fetal calf serum, DMEM medium (Virology, Vol. 8, 396 (1959)), RPMI 1640 medium (Journal of the American Medical Association, Vol. 199, 519 (1967)), 199 medium (Proceedings of the Society of the Biological Medicine, Vol. 73, 1 (1950)). Preferable pH of the medium is about 6 to about 8. The transformant is cultured usually at about 30–40° C. for about 15–60 hours. If necessary, aeration and stirring may be applied.

Thus, the polypeptide of the invention can be produced inside of transformant cells, in their cell membranes, or outside of these cells.

Separation and purification of the polypeptide from the resultant culture can be carried out, for example, according to the methods described below.

For extraction of the polypeptide of the invention from cultured microorganisms or cells, the microorganisms or cells are harvested by publicly known methods after the cultivation, suspended in a suitable buffer, and disrupted by sonication or by lysozyme and/or freezing and thawing, etc. Then, a crude extract of the polypeptide is obtained by centrifugation or filtration. The buffer may contain a protein denaturing agent such as urea or guanidine hydrochloride, or a surfactant such as Triton X-100™. If the polypeptide is secreted into the culture broth, the supernatant is separated from the microorganisms or cells after completion of the cultivation and collected by publicly known methods.

Purification of the polypeptide contained in the thus obtained culture supernatant or extract can be performed by an appropriate combination of publicly known methods for separation and purification. These publicly known methods include methods utilizing solubility such as salting out or sedimentation with solvents, methods mainly utilizing difference in molecular weight such as dialysis, ultrafiltration, gel filtration and SDS-polyacrylamide gel electrophoresis, methods utilizing difference in electric charge such as ion-exchange chromatography, methods utilizing specific affinity such as affinity chromatography, methods utilizing difference in the hydrophobicity such as reversed-phase high-performance liquid chromatography, and methods utilizing difference in isoelectric point such as isoelectric electrophoresis.

When the thus obtained polypeptide is a free form, the polypeptide can be converted into a salt by publicly known methods or methods based thereon. On the contrary, when the polypeptide is obtained in a salt form, the salt can be converted into a free form or another salt according to publicly known methods or methods based thereon.

The polypeptide produced by the transformant can be arbitrarily modified or a part thereof can be removed therefrom by using an appropriate protein modification enzyme or proteolytic enzyme before or after the purification. Examples of such enzymes include trypsin, chymotrypsin, arginyl endopeptidase, protein kinase and glycosidase.

The presence of the polypeptide of the invention thus obtained can be measured by enzyme immunoassay, Western blot analysis or the like using specific antibodies.

Antibodies to the polypeptide of the invention or salt thereof may be either polyclonal or monoclonal antibodies as long as they can recognize the polypeptide of the invention or salt thereof.

Antibodies to the polypeptide of the invention or salt thereof can be prepared using the polypeptide of the invention as antigen and according to publicly known producing methods for antibody or anti-serum preparation.

Preparation of Monoclonal Antibodies (a) Preparation of Monoclonal Antibody-Producing Cells The polypeptide of the invention or salt thereof is administered to warm-blooded animals either alone or together with a carrier or diluent to a site capable of producing antibodies upon the administration. In order to enhance the ability to produce antibodies, complete Freund's adjuvants or incomplete Freund's adjuvants may also be administered. The administration is usually carried out once in every two to six weeks and two to ten times in the total. Examples of warm-blooded animals utilized include monkey, rabbit, dog, guinea pig, mouse, rat, sheep, goat and chicken. Among them, mouse or rat is used preferably.

In the preparation of monoclonal antibody-producing cells, individuals with detectable antibody titers are selected from warm-blooded animals (e.g. mice) immunized with antigen. Then, the spleen or lymph nodes are collected from them two to five days after the final immunization, and antibody-producing cells contained therein are fused with myeloma cells of a homologous or heterologous animal to thereby obtain monoclonal antibody-producing hybridomas. Measurement of antibody titers in antisera may be carried out, for example, by reacting a labeled polypeptide, which will be described later, with the antiserum followed by measuring the activity of the labeling agent bound to the antibody. The cell fusion may be carried out by a known method, for example, the method of Koehler and Milstein (Nature, 256, 495, (1975)). Examples of fusion promoters include polyethylene glycol (PEG), Sendai virus, etc. Preferably, PEG is used.

Examples of myeloma cells include myeloma cells of warm-blooded animals such as NS-1, P3U1, SP2/0, AP-1, etc. Preferably, P3U1 is used. A preferable ratio of the number of antibody-producing cells used (spleen cells) to the number of myeloma cells is about 1:1 to 20:1. When PEG (preferably, PEG 1000 to PEG 6000) is added at a concentration of about 10–80% and the resultant cell mixture is incubated at 20–40° C. (preferably, at 30–37° C.) for about one to ten minutes, an efficient cell fusion can be performed.

Various methods may be used for screening for monoclonal antibody-producing hybridomas. For example, hybridoma culture supernatant is added to a solid phase (e.g. microplate) on which the polypeptide antigen has been adsorbed either directly or with a carrier. Then, a radioactively or enzymatically labeled anti-immunoglobulin antibody (anti-mouse immunoglobulin antibody is used when mouse cells are used in the cell fusion) or protein A is added thereto to detect monoclonal antibodies bound to the solid phase. Alternatively, a method may be used in which hybridoma culture supernatant is added to a solid phase on which an anti-immunoglobulin antibody or protein A has been adsorbed; then, a radioactively or enzymatically labeled polypeptide is added thereto to thereby detect monoclonal antibodies bound to the solid phase.

Selection of monoclonal antibodies may be carried out by publicly known methods or methods based on them. Usually, selection can be carried out in a medium for culturing animal cells supplemented with HAT (hypoxanthine, aminopterin and thymidine). As a medium for selection and culturing, any medium may be used as long as hybridomas are capable of growing therein. Examples of media include RPMI 1640 medium containing about 1–20% (preferably about 10–20%) of fetal calf serum, GIT medium (Wako Pure Chemical Industries, Ltd.) containing about 1–20% of fetal calf serum and a serum-free medium for hybridoma cultivation (SFM-101; Nissui Pharmaceutical Co.). The cultivation temperature is usually about 20–40° C., preferably about 37° C. The cultivation period is usually from five days to three weeks, preferably one to two weeks. The cultivation may be carried out usually under 5% carbon dioxide. The antibody titer of hybridoma culture supernatant may be measured in the same manner as in the above-mentioned measurement of the antibody titers in antisera.

(b) Purification of the Monoclonal Antibodies

Separation and purification of monoclonal antibodies may be carried out by publicly known methods, such as methods for separating/purifying immunoglobulin [e.g. salting-out, alcohol precipitation, isoelectric precipitation, electrophoresis, adsorption/desorption using ion exchangers (e.g. DEAE), ultracentrifugation, gel filtration, specific purification methods in which only an antibody is collected by means of an antigen-binding solid phase or active adsorbent such as protein A or protein G, followed by dissociation of the bond].

Preparation of Polyclonal Antibodies

The polyclonal antibody of the invention can be produced by publicly known methods or methods based on them. For example, an immunogen (antigen polypeptide) per se or a complex of the immunogen and a carrier protein is prepared. Then, using the immunogen or the complex, warm-blooded animals are immunized in the same manner as described for the production of monoclonal antibodies. Fractions containing the antibody against the polypeptide of the invention or salt thereof are harvested from the immunized animals, followed by separation and purification of the antibody.

With respect to the immunogen-carrier protein conjugate for use in the immunization of warm-blooded animals, the kind of carrier protein and the mixing ratio of the carrier and the hapten are not particularly restricted as long as antibodies are produced efficiently against the hapten cross-linked to the carrier. For example, bovine serum albumin, bovine thyroglobulin, hemocyanine, or the like is coupled to the hapten at a weight ratio of about 0.1–20:1, preferably about 1–5:1.

A variety of condensing agents can be used for the coupling between the hapten and the carrier. For example, glutaraldehyde, carbodiimide, maleimide, or active ester reagents containing a thiol or dithiopyridyl group may be used.

The condensation product is administered to a warm-blooded animal either alone or together with a carrier or diluent at a site capable of producing antibodies upon the administration. In order to enhance the antibody production ability, complete Freund's adjuvant or incomplete Freund's adjuvant may also be administered. Administration is carried out generally once in about every 2–6 weeks and about 3–10 times in the total.

Polyclonal antibodies can be recovered from the blood, abdominal dropsy or other body fluid, preferably from the blood, of the warm-blooded animal immunized as described above.

Polyclonal antibody titers in antisera can be determined in the same manner as described above for the determination of monoclonal antibody titers in antisera. The separation and purification of polyclonal antibodies can be carried by the same methods for separation and purification of immunoglobulin as those described for the separation and purification of monoclonal antibodies.

With respect to the antisense DNA having a base sequence complementary to or substantially complementary to a DNA encoding the polypeptide of the invention (hereinafter, sometimes referred to as the "DNA of the invention"), any antisense DNA may be used as long as it has a base sequence complementary to or substantially complementary to the DNA of the invention and is able to inhibit the expression of the DNA.

A base sequence substantially complementary to the DNA of the invention refers to, for example, a base sequence having about 70% or more, preferably about 80% or more, more preferably about 90% or more, most preferably about 95% or more homology to the full-length or partial base sequence of the complementary base sequence to the DNA of the invention (i.e., the complementary strand to the DNA of the invention). Particularly preferable is an antisense DNA having about 70% or more, preferably about 80% or more, more preferably about 90% or more, most preferably about 95% or more homology to a partial base sequence of the complementary strand to the DNA of the invention that is complementary to a base sequence encoding an N-terminal portion of the polypeptide of the invention (e.g. base sequence encoding a region adjacent to the initiation codon). These antisense DNAs can be synthesized with DNA synthesizers that are publicly known.

Hereinbelow, uses of the polypeptide of the invention, amide or ester thereof, or salt thereof (sometimes, they are simply referred to as the "polypeptide of the invention"); the DNA encoding the polypeptide of the invention (sometimes referred to as the "DNA of the invention"); the antibody to the polypeptide of the invention, amide or ester thereof, or salt thereof (sometimes referred to as the "antibody of the invention"); and the antisense DNA will be described.

(1) Therapeutic and/or Prophylactic for Various Diseases where Cubilin is Involved Cubilin exists as a membrane protein in vivo and binds to apolipoprotein A-I. The polypeptide of the invention, which is a partial fragment of cubilin having the ability to bind to apolipoprotein A-I, is able to repress the catabolism of apolipoprotein A-I by binding to apolipoprotein A-I contained in the blood. Therefore, the polypeptide and the DNA of the invention may be used as medicines such as therapeutics and/or prophylactics for diabetes, obesity, arteriosclerosis, hyperlipemia, hypertriglyceridemia, hypo-high density lipoproteinemia, hypoapolipoproteinemia A-I or nervous disorders. It is possible to allow the role of the polypeptide of the invention to manifest sufficiently in patients by, for example, (a) administering the DNA of the invention to patients and allowing the polypeptide of the invention to express in vivo; (b) inserting the DNA of the invention into cells, allowing the expression of the polypeptide of the invention therein, and transplanting the cells into patients; or (c) administering the polypeptide of the invention to patients.

When the DNA of the invention is used as the above-mentioned therapeutic and/or prophylactic agent, the DNA per se or the DNA inserted into an appropriate vector such as a retrovirus vector, adenovirus vector, adeno-associated virus vector, etc. may be administered to human or other warm-blooded animals using conventional means. The DNA of the invention or a vector into which the DNA of the invention is inserted may be administered as it is or after formulation with physiologically acceptable carriers such as adjuvants to promote uptake. Usually, the DNA or the vector may be administered parenterally by means of, e.g., a gene gun or a catheter such as hydrogel catheter.

When the polypeptide of the invention is used as the above-described therapeutic and/or prophylactic agent, at least 90%, preferably 95% or more, more preferably 98% or more, still preferably 99% or more purified polypeptide of the invention is used.

The polypeptide of the invention may be used, for example, orally in the form of tablets (sugar-coated, if necessary), capsules, elixirs, microcapsules or the like; or parenterally in the form of injections such as aseptic solutions or suspensions in water or other pharmaceutically acceptable liquids. These preparations may be produced, for example, by mixing the polypeptide of the invention with physiologically acceptable carriers, flavoring agents, excipients, vehicles, antiseptics, stabilizers, binders, etc. in unit dosage forms required for preparing generally approved pharmaceutical preparations. The amounts of active ingredients in these formulations are decided so that an appropriate dose within the specified range can be obtained.

Examples of additives miscible with tablets, capsules, etc. include binders such as gelatin, corn starch, tragacanth and gun arabic, excipients such as crystalline cellulose, swelling agents such as corn starch, gelatin and alginic acid, lubricants such as magnesium stearate, sweetening agents such as sucrose, lactose and saccharin, and flavoring agents such as peppermint, akamono oil and cherry. When the unit dosage form is capsule, liquid carrier such as oils and fats may further be included in addition to the above-mentioned materials. Sterile compositions for injection can be formulated according to conventional practices in pharmaceutical manufacturing, e.g., by dissolving or suspending active ingredients, naturally occurring vegetable oils such as sesame oil, coconut oil, etc. in vehicles such as water for injection.

Examples of aqueous liquids for injection include physiological saline and isotonic solutions containing glucose and other auxiliary agents (e.g. D-sorbitol, D-mannitol, sodium chloride, etc.). They may be used in combination with a suitable auxiliary solubilizer such as alcohol (e.g. ethanol, etc.), polyalcohol (e.g. propylene glycol, polyethylene glycol, etc.), nonionic surfactant (e.g. Polysorbate 80™, HCO-50, etc.). Examples of oily liquids for injection include sesame oil, soybean oil, etc. They may be used in combination with an auxiliary solubilizer such as benzyl benzoate, benzyl alcohol, etc. In addition, buffers (e.g. phosphate buffer, sodium acetate buffer, etc.), soothing agents (e.g. benzalkonium chloride, procaine hydrochloride, etc.), stabilizers (e.g. human serum albumin, polyethylene glycol, etc.), preservatives (e.g. benzyl alcohol, phenol, etc.), antioxidants, etc. may also be admixed therewith. Usually, the prepared injections are filled in appropriate ampoules.

Since the thus obtained preparations are safe and of low toxicity, they can be administered to human or other warm-blooded animals (e.g., rat, mouse, guinea pig, rabbit, avian, sheep, pig, bovine, horse, cat, dog, monkey, etc.).

Dose of the polypeptide of the invention may vary depending upon the target disease, the target to be administered, administration route, and so on. However, when the polypeptide of the invention is administered orally for treating diabetes, obesity, arteriosclerosis, hyperlipemia, hypertriglyceridemia, hypo-high density lipoproteinemia, hypoapolipoproteinemia A-I or nervous disorders, generally the polypeptide of the invention is administered to adult (60 kg in body weight) at a dose of about 1–1000 mg/day, preferably about 10–500 mg/day, more preferably about 10–200 mg/day. With respect to parenteral administration, when the polypeptide of the invention is administered to adult (60 kg in body weight) in the form of an injection for treating diabetes, obesity, arteriosclerosis, hyperlipemia, hypertriglyceridemia, hypo-high density lipoproteinemia, hypoapolipoproteinemia A-I or nervous disorders, it is convenient to inject the polypeptide of the invention into the affected part of the body at a dose of about 1–1000 mg/day, preferably about 1–200 mg/day, and more preferably about 10–100 mg/day, though the dose per administration may vary depending on the patient to be treated, the target disease, etc. For other animals, corresponding doses may be administered after conversion of the above-mentioned values per 60 kg based on actual body weights.

(2) Screening for Candidate Compounds for Medicine to Diseases (i) When the expression level of cubilin is abnormally enhanced, various diseases such as, for example, hyperlipemia, hypertriglyceridemia, hypo-high density lipoproteinemia, hypoapolipoproteinemia A-I, after meal hyperlipemia, diabetes, obesity, arteriosclerosis, myocardial infarction or angina occur.

Therefore, compounds or salts thereof that inhibit the binding of cubilin to apolipoprotein A-I may be used as medicines such as therapeutics and/or prophylactics for, e.g., hyperlipemia, hypertriglyceridemia, hypo-high density lipoproteinemia, hypoapolipoproteinemia A-I, after meal hyperlipemia, diabetes, obesity, arteriosclerosis, myocardial infarction or angina.

(ii) On the other hand, since cubilin exists as a membrane protein in vivo and binds to apolipoprotein A-I, various diseases such as renal disorders, nephritis, nephropathy, proteinuria, nervous disorders and vitamin $B_{12}$ deficiency occur when cubilin or DNA encoding the same is abnormal or deficient, or cubilin expression is abnormally reduced.

Therefore, compounds or salts thereof that promote the binding of cubilin to apolipoprotein A-I may be used as medicines such as therapeutics and/or prophylactics for various diseases such as renal disorders, nephritis, nephropathy, proteinuria, neurological disorders and vitamin $B_{12}$ deficiency.

Therefore, use of cubilin for screening for those compounds or salts thereof that inhibit or promote the function of cubilin can be contemplated.

However, since cubilin is a large protein consisting of more than 3,500 amino acids, non-specific adsorption or binding, or degradation of cubilin molecules per se may occur when cubilin molecules are used in the screening for such compounds or salts thereof; due to these drawbacks, it is impossible to carry out highly sensitive and efficient screening.

On the other hand, the screening method using the polypeptide of the invention does not have such drawbacks. By using this screening method, compounds or salts thereof that inhibit or promote the binding between the polypeptide of the invention and apo A-I can be screened with high sensitivity and efficiently. Since such compounds or salts thereof inhibit or promote the binding between cubilin and apo A-I, they can be used as medicines such as therapeutics and/or prophylactics for the above-mentioned various diseases.

That is, the present invention provides:

1) ① a method for screening for compounds or salts thereof that inhibit the binding between cubilin and apo A-I (sometimes abbreviated to "inhibitor(s)" in "(2) Screening for Candidate Compounds for Medicine to Treat Diseases") or compounds or salts thereof that promote the binding between cubilin and apo A-I (sometimes abbreviated to "promoter(s)" in "(2) Screening for Candidate Compounds for Medicine to Treat Diseases"), wherein the method is characterized by using the polypeptide of the invention; and ② a screening kit for inhibitors or promoters comprising the polypeptide of the invention (sometimes referred to as the "screening kit of the invention" in "(2) Screening for Candidate Compounds for Medicine to Treat Diseases"). More specifically, the present invention provides:

2) ① a method for screening for promoters or inhibitors, comprising comparing (i) the case where apo A-I is contacted with the polypeptide of the invention and (ii) the case where apo A-I and a test compound are contacted with the polypeptide of the invention; and ② a screening kit for promoters and inhibitors, comprising the polypeptide of the invention and apo A-I.

Specifically, the above-mentioned screening method is characterized by measuring and comparing the amounts of binding of apo A-I to the polypeptide of the invention or the amounts of binding of the polypeptide of the invention to apo A-I in the cases (i) and (ii).

These amounts of binding can be measured by publicly known methods or methods based on them.

Examples of test compounds include, but not limited to, peptides, proteins, non-peptidic compounds, synthetic compounds, fermentation products, cell extracts, plant extracts, and animal tissue extracts. These compounds may be either novel compounds or publicly known compounds.

As the peptide, partial peptides of apo A-I are preferable.

For example, a test compound that reduces the amount of binding in case (ii) above by about 20% or more, preferably 30% or more, more preferably about 50% or more compared to the amount of binding in case (i) above may be selected as a compound that inhibits the binding between cubilin and apo A-I. On the other hand, a test compound that increases the amount of binding in case (ii) above by about 20% or more, preferably 30% or more, more preferably about 50% or more compared to the amount of binding in case (i) above may be selected as a compound that promotes the binding between cubilin and apo A-I.

The compounds of salts thereof obtained by using the screening method or the screening kit of the invention are compounds that are selected from the above-mentioned test compounds, e.g. peptides, proteins, non-peptidic compounds, synthetic compounds, fermentation products, cell extracts, plant extracts, animal tissue extracts, plasma, etc., and that promote or inhibit the function of cubilin (e.g. binding to apolipoprotein A-I).

As salts of such compounds, salts same as those salts of the polypeptide of the invention described herein earlier may be used.

Hereinbelow, the screening method will be described specifically.

The screening may be performed by SPA (scintillation proximity assay) method (Anal. Biochem. 1987 March; 161 (2): 494–500), fluorescence binding assay, a method using a surface plasmon sensor, or a method based on them.

[I] SPA method may be performed as follows.

The polypeptide of the invention is bound to SPA beads directly or indirectly and then mixed with (i) apo A-I labeled with a radioactive isotope or (ii) apo A-I labeled with a radioactive isotope and a test compound. Subsequently, the fluorescence intensities in case (i) and case (ii) are measured and compared.

More specifically, the method is performed as follows:
①  The polypeptide of the invention is bound to SPA beads. The binding may be either direct or indirect.

As a method for direct binding, the method described in the protocol attached to SPA beads may be used. As a method for indirect binding, the following methods may be enumerated, for example:
(i) A method in which SPA beads coated with copper are used, and histidine tag-added polypeptide of the invention are bound to these SPA beads,
(ii) A method in which SPA beads coated with glutathione are used, and a fusion protein composed of GST and the polypeptide of the invention is bound to these SPA beads,
(iii) A method in which SPA beads coated with a secondary antibody are used, and the polypeptide of the invention and these SPA beads are bound via a linker that is an antibody to the polypeptide,
(iv) A method in which SPA beads coated with a secondary antibody are used, and the polypeptide of the invention to which a tag such as FLAG or myc has been added is bound to these SPA beads via an antibody to the tag,
(v) A method in which SPA beads coated with streptavidin are used, and biotin-labeled polypeptide of the invention is bound to these SPA beads,
(vi) A method in which SPA beads coated with streptavidin are used, and the polypeptide of the invention to which a tag such as FLAG or myc has been added is bound to these SPA beads via a linker that is a biotin-labeled antibody to the tag.

When the polypeptide of the invention has sugar chains, the following method may also be used:
(vii) A method in which SPA beads coated with WGA (wheat germ agglutinin) are used, and the polypeptide of the invention is bound to these SPA beads.

SPA beads coated with such materials may be prepared by publicly known methods or methods based on them. However, it would be convenient to purchase them from Amersham Pharmacia Biotech.

② (i) When a tag is added to the polypeptide of the invention, any conventional tag used in the art may be used as long as it can be detected specifically.

Preferable examples include tags consisting of several amino acids, such as FLAG and histidine tag that do not affect the binding between the polypeptide of the invention and apo A-I.

By expressing a fusion composed of such a tag and the polypeptide of the invention, a tag-added polypeptide of the invention can be obtained. The fusion can be obtained by inserting a DNA encoding the polypeptide of the invention into a vector such as pFLAG-CMV-1, pSecTag or pcDNA3.1/His, introducing the vector into an appropriate host cell such as $E.\ coli$, COS7 or CHO, and allowing the host cell to produce the polypeptide in cells or cell membranes or outside of cells. The tag may be added to any site of the polypeptide of the invention, but a site that does not affect the binding with apo A-I is preferable. Hereinafter, the polypeptide of the invention to which a tag has been added is sometimes referred to as "Tag-CUBIII".

(ii) A fusion protein composed of GST and the polypeptide of the invention can be prepared by publicly known methods or methods based on them. The site of fusion may be any site of the polypeptide of the invention, but a site that does not affect the binding with apo A-I is preferable.

(iii) When apo A-I is labeled with a radioactive isotope (e.g. [$^{125}$I], [$^{131}$I], [$^{3}$H], [$^{14}$C], [$^{35}$S] or [$^{33}$P]), the labeling may be performed by publicly known methods or methods based on them. Specifically, apo A-I is dissolved in 40 ml of 0.4 M glycine-NaOH buffer (pH 8.5) at 50 μg/ml, followed by addition of 1 mCi of $^{125}$I for labeling reaction. To the reaction solution, 50 μl of Cloramin T solution (4 mg/ml) is added and maintained at room temperature for 15 min. Then, 100 μl of metabisulfite solution (16 mg/ml) is added thereto and stirred for 10 min. The resultant reaction solution is extracted with 40 ml of acetone/diethyl ether (3:1, v/v). The resultant precipitate is dried, dissolved in a phosphate buffer and subjected to dialysis against the buffer to thereby obtain $^{125}$I-labeled apo A-I.

(iv) When an anti-tag antibody is modified with biotin, an anti-tag antibody may be prepared by publicly known methods or methods based on them using a tag such as FLAG or myc as an antigen. Such an antibody may be either a monoclonal antibody or a polyclonal antibody. Commercial anti-tag antibodies may also be used. As an anti-myc antibody, Clone 9E10 (Sigma) or the like may be used. As an anti-FLAG antibody, Clone M1 (Sigma) or the like may be used.

The modification of anti-tag antibodies and the polypeptide of the invention with biotin may be performed by publicly known methods or methods based on them. Specifically, an anti-tag antibody or the polypeptide of the invention is dissolved in a carbonate buffer (0.1 M sodium hydrogencarbonate, 0.1 M sodium chloride, pH 8.3) to give a concentration of 1 mg/ml. To this solution, 50 μl of an aqueous solution of Sulfo-NHS-Biotin (Pierce) (1 mg/ml) is added and mixed gently overnight at 4° C. Then, the reaction solution is dialyzed against 20 mM Tris-HCl buffer (pH 7.4) containing 150 mM sodium chloride to perform biotin modification.

(v) After the procedures described in (i) to (iv) have been completed, the fluorescence intensity is measured with a scintillator. If the fluorescence intensity is decreased by the addition of a test compound, the compound can be selected as an inhibitor. If the fluorescence intensity is increased by the addition of a test compound, the compound can be selected as a promoter.

Hereinbelow, operational procedures will be described more specifically. Briefly, 1 mg of streptavidin-yttrium silicate type SPA beads, 0.5 μl of biotin-modified myc monoclonal antibody (9E10; Sigma), 10–200 ng of purified polypeptide of the invention (CUBIII-myc-His fragment), 250,000 cmp of radioactive iodine-labeled apo A-I, and 10 pmol to 100 pmol of unlabeled apo A-I are mixed in 20 mM Tris-HCl buffer (pH 7.4) containing 150 mM sodium chloride, 1.0 mM calcium chloride and 0.1% sodium azide (hereinafter, referred to as the "binding reaction buffer") to give a reaction solution of 200 μl.

This reaction solution is mixed gently at 25° C. for 1 hr and centrifuged in a bench type centrifuge at 1,000 rpm for 2 min to precipitate SPA beads. Then, the fluorescence emitted by SPA beads is measured with a scintillation counter. For the purpose of evaluation of substances that inhibit or promote binding, a test substance is dissolved in the above-mentioned binding reaction buffer and included in a 200 μl reaction solution. Substances that change scintillation counts are evaluated taking the scintillation count in the absence of the test substance as 100%.

The screening kit of the invention comprises labeled apo A-I, variously coated SPA beads and the polypeptide of the invention.

[II] Fluorescence apo A-I binding assay is performed using a plate coated with the fragment peptide of the invention.

Specifically, the assay is performed as described below. After the polypeptide of the invention is solidified in a plate, labeled apo A-I and a test compound are mixed and incubated on the plate. After washing, the amount of labeled apo A-I bound to the polypeptide is determined by an appropriate method.

For example, the polypeptide of the invention is diluted to 0.1–10 μg/ml in a buffer and solidified by incubation in a high binding ability-type microplate for fluorescence measurement (e.g. Black Clini plate enhanced binding; Labsystems). As the buffer, a buffer containing 20 mM Tris-HCl (pH 7.4), 500 mM NaCl, 2 mM $CaCl_2$ and 0.1% sodium azide may be used, for example.

After the polypeptide is solidified by an overnight or longer incubation, non-specific binding is inhibited with an appropriate blocking reagent. For this purpose, SuperBlock TBS (Pierce) may be used, for example.

After this blocking, the microplate is washed with a buffer to be used in the subsequent binding reaction. Then, a mixture of labeled apo A-I and a test compound is incubated on wells of the microplate to carry out competitive binding reaction. As the buffer, a buffer containing 20 mM Tris-HCl (pH 7.4), 150 mM NaCl, 1 mM $CaCl_2$, 0.1% sodium azide and 5% Block-Ace (Dainippon Pharmaceutical) may be used, for example. For labeling apo A-I particles, Sulfo-NHS-LC-LC-Biotin may be used, for example. Specifically, apo A-I is dissolved in 50 mM sodium bicarbonate (pH 8.5) at a concentration of 1 mg/ml. To this solution, 1/10 volume of Sulfo-NHS-LC-LC-Biotin dissolved in pure water at 1 mg/ml is added and incubated overnight at 4° C. to thereby prepare biotin-labeled apo A-I. As the concentration of biotin-labeled apo A-I in the competitive binding reaction solution, a concentration of approximately 0.1 μg/ml may be used, for example.

For quantitative determination of biotin-labeled apo A-I bound to the polypeptide after washing, β-galactosidase-labeled streptavidin may be used, for example. For measuring its activity, 4-methylumbelliferyl-β-D-galactopyranoside or the like may be used. In this case, the amount of biotin-labeled apo A-I specifically bound to the polypeptide of the invention can be calculated and determined by measuring excitation light at around 365 nm and fluorescence emission at around 460 nm.

[III] The method using a surface plasmon sensor may be performed using BIACORE™ 3000 (Biacore) or the like according to the protocol attached thereto. Specifically, this method may be performed as described below.

The polypeptide of the invention is bound to a sensor chip directly or indirectly, and (i) apo A-I solution is applied to the sensor chip; or (ii) apo A-I solution containing a test substance is applied to the sensor chip. Then, the surface plasmon values in the cases of (i) and (ii) are measured and compared.

If the fluorescence intensity is decreased by the addition of a test compound, the compound can be selected as an inhibitor. If the fluorescence intensity is increased by the addition of a test compound, the compound can be selected as a promoter.

More specifically:

① The polypeptide of the invention is fixed on the sensor chip. This fixing may be either direct fixing or indirect fixing.

Direct fixing may be performed by any binding method. Preferably, the polypeptide is fixed on the sensor chip by covalent bond as NHS-ester. As a method for indirect fixing, a method based on the above-mentioned method may be used.

Alternatively, apo A-I may be fixed on a sensor chip, and a solution of the polypeptide of the invention may be applied to the sensor chip.

② Subsequently, apo A-I solution is applied to the sensor chip.

③ The surface plasmon is measured.

Specifically, a sensor chip CM5 is treated with a 1:1 mixture of 0.2 M n-ethyl-N'-(3-dimethylaminopropyl)-carbodiimide aqueous solution and 0.05 M N-hydroxysuccinimide aqueous solution. To this sensor chip, the polypeptide of the invention (CUBIII-myc-His fragment) dissolved in 10 mM sodium acetate (pH 4.0) at 40 μg/ml is applied to thereby fix the polypeptide of the invention to censor chip CM5. For blocking, 1 M ethanol amine (pH 8.5) is applied. As a buffer for measuring binding, a buffer containing 10 mM sodium dihydrogen phosphate, 150 mM sodium chloride, 1.0 mM calcium chloride and 0.1% sodium azide (pH 7.4) is used. After equilibration with this buffer and stabilization of plasmon changes, apo A-I diluted with this buffer to 50–500 nM is applied to the sensor chip to measure changes in surface plasmon. For the purpose of evaluation of substances that inhibit or promote the binding, a test substance is dissolved in the above-described buffer and mixed with the apo A-I solution. By comparing changes in surface plasmon in the absence of a test compound with changes in the presence of the test compound, binding inhibitors or promoters are evaluated.

The screening kit of the invention comprises a sensor chip on which the polypeptide of the invention or apo A-I is fixed, and apo A-I or the polypeptide.

Compounds or salts thereof that are obtainable by using the screening method or screening kit of the invention are those compounds that are selected from, for example, peptides, proteins, non-peptidic compounds, synthetic compounds, fermentation products, cell extracts, plant extracts, animal tissue extracts and plasma, and that promote or inhibit the function of the polypeptide of the invention.

As salts of such compounds, salts same as those salts of the polypeptide of the invention described herein earlier may be used.

When the compound obtained by using the screening method or screening kit of the invention is used as the above-mentioned therapeutic and/or prophylactic agent, it may be used according to conventional procedures. For example, the compound may be formulated into tablets, capsules, elixirs, microcapsules, aseptic solutions, suspensions, etc. in the same manner as described in the preparation of medicines comprising the polypeptide of the invention.

Since the thus obtained pharmaceutical preparations are safe and of low toxicity, they can be administered to human or other warm-blooded animals (e.g., mouse, rat, rabbit, sheep, pig, bovine, horse, avian, cat, dog, monkey, etc.).

Dose levels of the compound or salt thereof may vary depending upon the target disease, the target to be administered, administration route, and so on. However, when a compound that promotes the binding between the polypeptide of the invention and apo A-I is administered orally for treating nephritis, nephropathy, hyper-high density lipoproteinemia, hyperapolipoproteinemia A-I or proteinuria, generally the compound is administered to adult (60 kg in body weight) at a dose of about 0.1–100 mg/day, preferably about 1.0–50 mg/day, more preferably about 1.0–20 mg/day. With respect to parenteral administration, when a compound that promotes the binding between the polypeptide of the invention and apo A-I is administered to adult (60 kg in body weight) in the form of an injection for treating nephritis, nephropathy, hyper-high density lipoproteinemia, hyperapolipoproteinemia A-I or proteinuria, it is convenient to inject the compound intravenously at a dose of about 0.01–30 mg/day, preferably about 0.1–20 mg/day, and more preferably about 0.1–10 mg/day, though the dose per administration may vary depending on the target to be administered, the target disease, etc. For other animals, corresponding doses may be administered after conversion of the above-mentioned values per 60 kg based on actual body weights.

On the other hand, when a compound that inhibits the binding between the polypeptide of the invention and apo A-I is administered orally for treating diseases such as hyperlipemia, hypertriglyceridemia, hypo-high density lipoproteinemia, hypoapolipoproteinemia A-I, after meal hyperlipemia, arteriosclerosis, myocardial infarction or angina, generally the compound is administered to adult (60 kg in body weight) at a dose of about 0.1–100 mg/day, preferably about 1.0–50 mg/day, more preferably about 1.0–20 mg/day. With respect to parenteral administration, when a compound that inhibits the binding between the polypeptide of the invention and apo A-I is administered to adult (60 kg in body weight) in the form of an injection for treating diseases such as hyperlipemia, hypertriglyceridemia, hypo-high density lipoproteinemia, hypoapolipoproteinemia A-I, after meal hyperlipemia, arteriosclerosis, myocardial infarction or angina, it is convenient to inject the compound intravenously at a dose of about 0.01–30 mg/day, preferably about 0.1–20 mg/day, and more preferably about 0.1–10 mg/day, though the dose per administration may vary depending on the target to be administered, the target disease, etc. For other animals, corresponding doses may be administered after conversion of the above-mentioned values per 60 kg based on actual body weights.

(3) Quantitative Determination of the Polypeptide of the Invention or Salt Thereof Since an antibody to the polypeptide of the invention (hereinafter, sometimes referred to as the "antibody of the invention") can specifically recognize the polypeptide of the invention and cubilin (hereinafter, sometimes referred to as the "polypeptide of the invention" in "(4) Quantitative Determination of the Polypeptide of the Invention of Salt Thereof"), the antibody may be used for quantitative determination of the polypeptide of the invention contained in a sample solution. In particular, the antibody may be used in quantitative determination by sandwich immunoassay technique.

The present invention provides:

(i) a method of quantitative determination of the polypeptide of the invention in a sample solution, comprising reacting the antibody of the invention with the sample solution and the polypeptide of the invention labeled, competitively and determining the ratio of the labeled polypeptide of the invention bound to the antibody; and (ii) a method of quantitative determination of the polypeptide of the invention in a sample solution, comprising reacting the sample solution with the antibody of the invention insolubilized on a carrier and another antibody of the invention labeled, simultaneously or in succession and determining the activity of the label on the insolubilized carrier.

A monoclonal antibody to the polypeptide of the invention (hereinafter, sometimes referred to as the "monoclonal antibody of the invention") may be used to quantitatively determine the polypeptide of the invention or may be used for detection of the polypeptide by tissue staining. For these purposes, either antibody molecules per se or the F(ab')$_2$, Fab' or Fab fragment thereof may be used.

Methods of quantitative determination of the polypeptide of the invention using the antibody of the invention are not particularly limited. Any measuring method may be used in which the amount of antibody, antigen or antibody-antigen complex corresponding to the amount of the antigen in a sample solution (e.g. the amount of the polypeptide of the invention) is detected by chemical of physical means, and then calculated from a standard curve prepared with a standard solution containing a known amount of the antigen. For example, nephrometry, competitive method, immunometric method and sandwich method may be used suitably and, in terms of sensitivity and specificity, the sandwich method described later is particularly preferred.

Examples of labeling agents used in measuring methods utilizing labeling substances include radioisotopes, enzymes, fluorescent substances, and luminescent substances. Examples of radioisotopes include [$^{125}$I], [$^{131}$I], [$^{3}$H] and [$^{14}$C]. Preferred examples of enzymes are those which are stable and with high specific activity, e.g., β-galactosidase, β-glucosidase, alkali phosphatase, peroxidase and malate dehydrogenase. Examples of fluorescent substances include fluorescamine and fluorescein isothiocyanate. Examples of luminescent substances include luminol, luminol derivatives, luciferin, and lucigenin. Further, a biotin-avidin system may also be used for binding an antibody or antigen with a labeling agent.

Insolubilization of antigens or antibodies may be performed by physical adsorption or by chemical binding usually used for insolubilizing or immobilizing polypeptides or enzymes. Examples of carriers include insoluble polysaccharides such as agarose, dextran and cellulose; synthetic resins such as polystyrene, polyacrylamide and silicone; and glass.

In sandwich method, a sample solution is reacted with an insolubilized monoclonal antibody of the invention (primary reaction); then, another monoclonal antibody of the invention that is labeled is reacted therewith (secondary reaction); and the activity of the labeling agent on the insolubilized carrier is measured to thereby quantitatively determine the amount of the polypeptide of the invention in the sample solution. The primary reaction and the secondary reaction may be conducted in a reverse order, or they may be conducted simultaneously or with an interval. The type of the labeling agent and the method of insolubilization may be the same as those described herein earlier. In immunoassays using the sandwich technique, the antibody insolubilized on a solid phase or the antibody labeled is not necessarily a single antibody; a mixture of two or more antibodies may be used for the purposes of enhancing the sensitivity of measurement, etc.

In the method of measuring the polypeptide of the invention by the sandwich method of the invention, the monoclonal antibodies of the invention used in the primary and the secondary reactions are preferably those antibodies wherein their sites binding of the polypeptide of the invention are different from each other. For example, if the antibody used in the secondary reaction recognizes the C-terminal region of the polypeptide of the invention, an antibody that recognizes a site other than the C-terminal region, e.g. an N-terminal region, is preferably used in the primary reaction.

The monoclonal antibody of the invention may be used in a measuring system other than the sandwich method, such as competitive methods, immunometric methods and naphrometry.

In competitive methods, an antigen in a sample solution and a labeled antigen are reacted competitively with an antibody; then, unreacted labeled antigen (F) and labeled antigen bound to the antibody (B) are separated (i.e. B/F separation); and the amount of the label of B or F to thereby quantitatively determine the amount of the antigen in the sample solution. With respect to this reaction method, there are a liquid phase method in which a soluble antibody is used and the B/F separation is conducted with polyethylene glycol and a second antibody to the above-mentioned antibody; and a solid phase method in which a solidified antibody is used as the first antibody or a soluble antibody is used as the first antibody while a solidified antibody is used as the second antibody.

In immunometric methods, an antigen in a sample solution and a solidified antigen are reacted competitively with a specific amount of a labeled antibody, followed by separation of the solid phase from the liquid phase; or an antigen in a sample solution is reacted with an excessive amount of a labeled antibody, and then a solidified antigen is added to bind unreacted labeled antibody to the solid phase, followed by separation of the solid phase from the liquid phase. Subsequently, the amount of label in one of the phases is measured to determine the amount of the antigen in the sample solution.

In nephrometry, the amount of insoluble precipitate generated as a result of antigen-antibody reaction in a gel or solution is measured. Even when the amount of the antigen in a sample solution is small and thus only a small amount of such precipitate is obtained, laser nephrometry utilizing the scattering of laser can be used suitably.

In applying each of those immunological measuring methods to the measuring method of the present invention, no special conditions or operations are required. A measuring system for the polypeptide of the present invention may be constructed using the conventional conditions and operational procedures in the relevant measuring method while taking into account usual technical consideration of those skilled in the art. For details of these commonly used technical means, a variety of reviews, reference books, etc. may be referred to.

For example, Hiroshi Irie (ed.): "Radioimmunoassay" (Kodansha, 1974); Hiroshi Irie (ed.): "Radioimmunoassay; Second Series" (Kodansha, 1979); Eiji Ishikawa et al. (ed.): "Enzyme Immunoassay" (Igaku Shoin, Japan, 1978); Eiji Ishikawa et al. (ed.): "Enzyme Immunoassay" (Second Edition) (Igaku Shoin, 1982); Eiji Ishikawa et al. (ed.): "Enzyme Immunoassay" (Third Edition) (Igaku Shoin, 1987); "Methods in Enzymology", Vol. 70 (Immunochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (Academic Press) and the like may be referred to.

By using the antibody of the invention as described above, the polypeptide of the invention can be quantitatively determined with high sensitivity.

Further, by quantitatively determining the concentration of the polypeptide of the invention using the antibody of the invention, it is possible to diagnose that a subject has a disease such as, e.g., hyperlipemia, hypertriglyceridemia, hypo-high density lipoproteinemia, hypoapolipoproteinemia A-I, after meal hyperlipemia, arteriosclerosis, myocardial infarction or angina, or that a subject is very likely to develop such a disease in the future, when an increase of decrease is detected in the concentration of the polypeptide of the invention in the subject.

Further, the antibody of the invention may be used for detecting the polypeptide of the invention present in body fluid, tissue or other samples. The antibody of the invention may also be used in the preparation of antibody columns for use in the purification of the polypeptide of the invention; in the detection of the polypeptide of the invention in individual fractions generated in the course of purification; and in the analysis of the behavior of the polypeptide of the invention in test cells.

(4) Gene Diagnostic Agent

When used as a probe, the DNA of the invention can detect abnormalities (gene abnormalities) in DNA or mRNA encoding the polypeptide of the invention in human or other warm-blooded animals (e.g. rat, mouse, guinea pig, rabbit, avian, sheep, pig, bovine, horse, cat, dog, monkey, etc.). Thus, the DNA of the invention is useful as a gene diagnostic agent for, e.g., damage, mutations or reduced expression of the DNA or mRNA encoding the polypeptide of the invention, or increase or excessive expression of the DNA or mRNA.

Gene diagnosis using the DNA of the invention described above, may be performed by publicly known methods such as Northern hybridization or PCR-SSCP method (Genomics, Vol. 5, 874–879 (1989); Proc. Natl. Acad. Sci. USA 86: 2766–2770 (1989)).

When a reduction in expression is detected by Northern hybridization or when mutations are detected in the DNA by PCR-SSCP method, for example, it is possible to diagnose that the relevant subject is very likely to have a disease such as renal disorders, nephritis, nephropathy, proteinuria, nervous disorders, or vitamin $B_{12}$ deficiency.

On the other hand, when excessive expression is detected by Northern hybridization, it is possible to diagnose that the relevant subject has a disease such as, e.g., hyperlipemia, hypertriglyceridemia, hypo-high density lipoproteinemia, hypoapolipoproteinemia A-I, after meal hyperlipemia, arteriosclerosis, myocardial infarction or angina.

(5) Medicines Containing the Antibody of the Invention

The antibody of the invention that neutralizes the activity of the polypeptide of the invention may be used as a therapeutic and/or prophylactic agent for, e.g., diseases caused by excessive expression of the polypeptide of the invention.

The neutralizing antibody of the invention specifically recognizes the apo A-I-binding site in cubilin or regions in the vicinity thereof. Therefore, like the inhibitor, the antibody may be used as medicines such as therapeutics and/or prophylactics for diseases such as, e.g., hyperlipemia, hypertriglyceridemia, hypo-high density lipoproteinemia, hypoapolipoproteinemia A-I, after meal hyperlipemia, arteriosclerosis, myocardial infarction or angina.

For these purposes, either antibody molecules per se or the F(ab')$_2$, Fab' or Fab fragment thereof may be used.

Therapeutics and/or prophylactics for the above-mentioned diseases comprising the antibody of the invention may be administered orally or parenterally to human or other warm-blooded animals (e.g., rat, rabbit, sheep, pig, bovine, cat, dog, monkey, etc.) in the form of a liquid preparation without any processing or in appropriate forms of pharmaceutical compositions. Dose levels may vary depending upon the patient to be treated, the target disease, symptoms, administration route, and so on. However, for the purpose of treating diseases such as hyperlipemia, hypertriglyceridermia, hypo-high density lipoproteinemia, hypoapolipoproteinemia A-I, after meal hyperlipemia, arteriosclerosis, myocardial infarction or angina, it is convenient to inject the antibody of the invention intravenously at a dose of about 0.01–20 mg/kg body weight, preferably about 0.1–10 mg/kg body weight, more preferably about 0.1–5 mg/kg body weight per administration about one to five times a day, preferably about one to three times a day. In other parenteral administration and oral administration, similar dose levels may be used. If symptoms are particularly heavy, the dose may be increased accordingly.

The antibody of the invention may be administered per se or in the forms of appropriate pharmaceutical compositions. The pharmaceutical compositions for the above administration comprise the antibody or salt thereof, pharmacologically acceptable carriers, and diluents or excipients. Such compositions are provided in forms appropriate for oral or parenteral administration.

For example, compositions for oral administration include solid or liquid preparations such as tablets (including sugar-coated tablets and film-coated tablets), pills, granules, dispersants, capsules (including soft capsules), syrups, emulsions and suspensions. These compositions are prepared according to conventional methods and contain carriers, diluents or excipients conventionally used in the field of medicine manufacture. For example, lactose, starch, sucrose, magnesium stearate and the like are used as carriers or excipients for tablets.

Compositions for parenteral administration include, for example, injections and suppositories. Injections include intravenous injections, subcutaneous injections, intradermal injections, muscle injections, instilment injections, etc. Such injections may be prepared by dissolving, suspending or emulsifying the above antibody or salt thereof in an aseptic, aqueous or oily liquid. Examples of aqueous liquids for injection include physiological saline and isotonic solutions containing glucose and other auxiliary agents. They may be used in combination with a suitable auxiliary solubilizer such as alcohol (e.g. ethanol), polyalcohol (e.g. propylene glycol, polyethylene glycol), nonionic surfactant [e.g. Polysorbate 80™, HCO-50 (polyoxyethylene (50 mol) adduct of hydrogenated castor oil)], etc.). Examples of oily liquids for injection include sesame oil and soybean oil. They may be used in combination with an auxiliary solubilizer such as benzyl benzoate, benzyl alcohol, etc. Usually, the prepared injections are filled in appropriate ampoules.

It is convenient to formulate the above-described pharmaceutical compositions for oral or parenteral administration into unit dosage forms that would give an appropriate dose of the active ingredient. Examples of such unit dosage forms include tablets, pills, capsules, injections (ampoules), and suppositories. Usually, each unit of these dosage forms contains preferably about 5–500 mg of the above-described antibody. In particular, each unit contains preferably about 5–100 mg in injections, and each unit in other dosage forms contains preferably about 10–250 mg.

The above-described pharmaceutical compositions may contain other active ingredients as long as they do not produce undesirable interaction with the above-described antibody.

In the specification and drawings of the present application, the abbreviations used for bases, amino acids and so forth are those recommended by the IUPAC-IUB Commission on Biochemical Nomenclature or those conventionally used in the art. Examples of such abbreviations are given below. Amino acids, which may have optical isomers are intended to represent their L-isomer unless otherwise specified.

DNA: Deoxyribonucleic acid
cDNA: Complementary deoxyribonucleic acid
A: Adenine
T: Thymine
G: Guanine
C: Cytosine
RNA: Ribonucleic acid
mRNA: Messenger ribonucleic acid
dATP: Deoxyadenosine triphosphate
dTTP: Deoxythymidine triphosphate
dGTP: Deoxyguanosine triphosphate
dCTP: Deoxycytidine triphosphate
ATP: Adenosine triphosphate
EDTA: Ethylenediaminetetracetic acid
SDS: Sodium dodecyl sulfate
Gly: Glycine
Ala: Alanine
Val: Valine
Leu: Leucine
Ile: Isoleucine
Ser: Serine
Thr: Threonine
Cys: Cysteine
Met: Methionine
Glu: Glutamic acid
Asp: Aspartic acid
Lys: Lysine
Arg: Arginine
His: Histidine
Phe: Phenylalanine
Tyr: Tyrosine
Trp: Tryptophan
Pro: Proline
Asn: Asparagine
Gln: Glutamine
pGlu: Pyroglutamic acid The substituents, protective groups and reagents that are frequently used in the specification are represented by the following abbreviations.
Me: Methyl group
Et: Ethyl group
Bu: Butyl group
Ph: Phenyl group
TC: Thiazolidine-4(R)-carboxamide group
Tos: p-Toluene sulfonyl
CHO: Formyl
Bzl: Benzyl
$Cl_2$-Bzl: 2,6-Dichlorobenzyl
Bom: Benzyloxymethyl
Z: Benzyloxycarbonyl
Cl-Z: 2-Chlorobenzyloxycarbonyl
Br-Z: 2-Bromobenzyloxycarbonyl
Boc: t-Butoxycarbonyl
DNP: Dinitrophenol
Trt: Trityl
Bum: t-Butoxymethyl
Fmoc: N-9-Fluorenylmethyloxycarbonyl
HOBt: 1-Hydroxybenzotriazole
HOOBt: 3,4-Dihydro-3-hydroxy-4-oxo-1,2,3-benzotriazine
HONB: 1-Hydroxy-5-norbornene-2,3-dicarboximide
DCC: N,N'-Dicyclohexylcarbodiimide The SEQ ID NOS of the SEQUENCE LISTING of the present specification represent the sequences as indicated below.

[SEQ ID NO: 1]
This shows the base sequence of a sense-strand primer used in Example 1.
[SEQ ID NO: 2]
This shows the base sequence of an antisense-strand primer used in Example 1.
[SEQ ID NO: 3]
This shows the base sequence of a sense-strand primer used in Example 1.
[SEQ ID NO: 4]
This shows the base sequence of an antisense-strand primer used in Example 1.
[SEQ ID NO: 5]
This shows the base sequence of a cDNA encoding a cubilin partial peptide obtained in Example 1.
[SEQ ID NO: 6]
This shows the base sequence of a cDNA encoding a cubilin partial peptide obtained in Example 1.
[SEQ ID NO: 7]
This shows the base sequence of a sense-strand primer used in Example 1.
[SEQ ID NO: 8]
This shows the base sequence of an antisense-strand primer used in Example 1.
[SEQ ID NO: 9]
This shows the base sequence of a cDNA encoding partial fragment III of human cubilin.
[SEQ ID NO: 10]
This shows the amino acid sequence of partial fragment III of human cubilin.
[SEQ ID NO: 11]
This shows the base sequence of a sense-strand primer used in Example 1.
[SEQ ID NO: 12]
This shows the base sequence of an antisense-strand primer used in Example 1.
[SEQ ID NO: 13]
This shows the base sequence of a sense-strand primer used in Example 1.
[SEQ ID NO: 14]
This shows the base sequence of an antisense-strand primer used in Example 1.
[SEQ ID NO: 15]
This shows the base sequence of a sense-strand primer used in Example 1.
[SEQ ID NO: 16]
This shows the base sequence of an antisense-strand primer used in Example 1.
[SEQ ID NO: 17]
This shows the base sequence of a sense-strand primer used in Example 1.
[SEQ ID NO: 18]
This shows the base sequence of an antisense-strand primer used in Example 1.
[SEQ ID NO: 19]
This shows the amino acid sequence of fragment peptide CUB9–CUB14 that is a partial fragment of human cubilin.
[SEQ ID NO: 20]
This shows the base sequence of a cDNA encoding fragment peptide CUB7–CUB12 that is a partial fragment of human cubilin.
[SEQ ID NO: 21]
This shows the amino acid sequence of a polypeptide used in Example 5.
[SEQ ID NO: 22]
This shows the base sequence of a cDNA encoding fragment peptide CUB9–CUB14 that is a partial fragment of human cubilin.

A transformant *Escherichia coli* DH5α/pTB2116 obtained in Example 1 has been deposited at the International Patent Organism Depositary, National Institute of Advanced Industrial Science and Technology, located at Central 6, 1—1 Higashi 1-chome, Tsukuba, Ibaraki under the Accession No. FERM BP-7190 since Jun. 19, 2000, and at the Institute for Fermentation, Osaka (IFO), located at 17–85 Jusanboncho 2-chome, Yodogawa-ku, Osaka, Osaka under the Accession No. IFO 16438 since Jun. 1, 2000.

Another transformant *Escherichia coli* DH5α/pTB2231 obtained in Example 4 has been deposited at the International Patent Organism Depositary, National Institute of Advanced Industrial Science and Technology, located at Central 6, 1—1 Higashi 1-chome, Tsukuba, Ibaraki under the Accession No. FERM BP-7607 since May 24, 2001, and at the Institute for Fermentation, Osaka (IFO), located at 17–85 Jusanboncho 2-chome, Yodogawa-ku, Osaka, Osaka under the Accession No. IFO 16626 since May 17, 2001.

EXAMPLES

The present invention will be described in more detail with reference to the following Examples. These Examples are provided only for explanation, and are not intended to limit the scope of the present invention.

Example 1

Cloning of cDNAs Encoding Partial Fragments of Human Cubilin

Using a human small intestine-derived cDNA library, cDNAs encoding partial fragments of human cubilin were cloned by PCR as described below.

A PCR reaction was performed using Marathon Ready cDNA (Clontech) derived from human small intestine, the oligo DNA shown in SEQ ID NO: 1 as a sense strand primer and the oligo DNA shown in SEQ ID NO: 2 as an anti-sense strand primer to thereby obtain a cDNA (SEQ ID NO: 5)

encoding a partial peptide of human cubilin. A cDNA (SEQ ID NO: 6) encoding a partial peptide of human cubilin was obtained in the same manner by PCR using the oligo DNA shown in SEQ ID NO: 3 as a sense strand primer and the oligo DNA shown in SEQ ID NO: 4 as an anti-sense strand primer. Then, the cDNA having the base sequence as shown in SEQ ID NO: 5 and the cDNA having the base sequence as shown in SEQ ID NO: 6 were mixed. Using this mixture as a template, a PCR reaction was performed with the oligo DNA shown in SEQ ID NO: 7 as a sense strand primer and the oligo DNA shown in SEQ ID NO: 8 as an anti-sense strand primer. After digestion with restriction enzymes BamfHI and NotI, the PCR product was inserted into a vector pSecTag2 (Invitrogen) pre-treated with the same restriction enzymes. As a result, a 2781 bp cDNA shown in SEQ ID NO: 9 encoding partial fragment III of human cubilin [SEQ ID NO: 10; a fragment having the amino acid sequence consisting of the amino acids from position 1165 to position 2091 of the amino acid sequence of human cubilin mature protein (FIGS. 1 and 2). This fragment corresponds to fragment peptide CUB7–CUB14.] was cloned into the vector that is an eukaryotic expression vector where Igκ signal sequence has been added to an upstream region and Myc and His tags have been added to a downstream region.

Similarly, using a cDNA obtained from Caco-2 cell-derived purified mRNA by RT-PCR with random primers, a PCR reaction was performed with the oligo DNA shown in SEQ ID NO: 11 as a sense strand primer and the oligo DNA shown in SEQ ID NO: 12 as an anti-sense strand primer to thereby obtain a cDNA encoding partial fragment I [a fragment having the amino acid sequence consisting of the amino acids from position 25 to position 816 of the amino acid sequence of human cubilin mature protein (FIGS. 1 and 2)]. A cDNA encoding partial fragment II [a fragment having the amino acid sequence consisting of the amino acids from position 474 to position 1390 of the amino acid sequence of human cubilin mature protein (FIGS. 1 and 2)] was obtained in the same manner using the oligo DNA shown in SEQ ID NO: 13 as a sense strand primer and the oligo DNA shown in SEQ ID NO: 14 as an anti-sense strand primer. These cDNAs were individually cloned into the above-described expression vector.

Further, using a human small intestine-derived Marathon Ready cDNA (Clontech), a PCR reaction was performed similarly with the oligo DNA shown in SEQ ID NO: 15 as a sense strand primer and the oligo DNA shown in SEQ ID NO: 16 as an anti-sense strand primer to thereby obtain a cDNA encoding partial fragment IV [a fragment having the amino acid sequence consisting of the amino acids from position 1852 to position 2804 of the amino acid sequence of human cubilin mature protein (FIGS. 1 and 2)]. A cDNA encoding partial fragment V [a fragment having the amino acid sequence consisting of the amino acids from position 2569 to position 3623 of the amino acid sequence of human cubilin mature protein (FIGS. 1 and 2)] was obtained in the same manner using the oligo DNA shown in SEQ ID NO: 17 as a sense strand primer and the oligo DNA shown in SEQ ID NO: 18 as an anti-sense strand primer. These cDNAs were individually cloned into the above-described expression vector.

Further, a plasmid pTB2116 obtained by integrating the cDNA (SEQ ID NO: 9) encoding a partial fragment III of human cubilin into pSecTag2 vector as described above was introduced into *Escherichia coli* DH5α according to publicly known methods to thereby obtain a transformant designated *Escherichia coli* DH5α/pTB2116.

Example 2

Expression of Human Cubilin Partial Fragments in COS7 Cells

Figure 3:
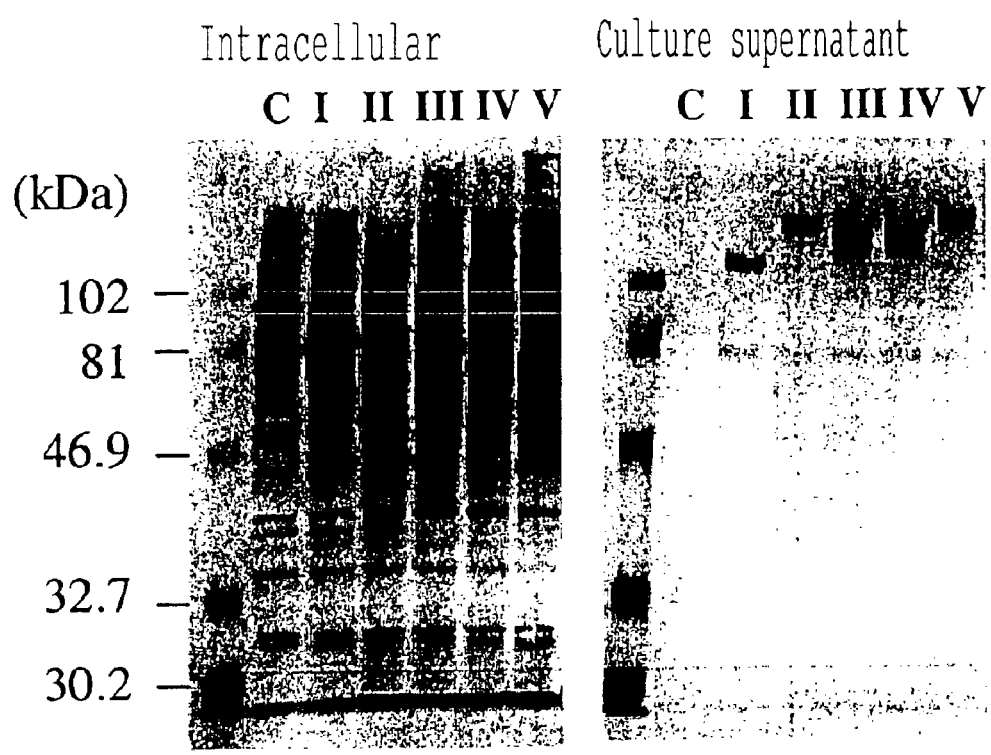
FIG. 3 shows the results of Western blotting carried out in Example 2. In this Figure, lane C shows pSecTag2-transfected COS7 cells; lanes I and II show COS7 cells transfected with expression vectors comprising pSecTag2 plasmids into which cDNAs encoding human cubilin partial fragments I and II are incorporated, respectively; lane III shows the culture supernatant from pTB2116-transfected COS cells; and lanes IV and V show COS7 cells transfected with expression vectors comprising pSecTag2 plasmids into which cDNAs encoding human cubilin partial fragments IV and V are incorporated, respectively. "Intracellular" denotes PVDF membranes blotted from those gels on which disrupted materials from individual cells were electrophoresed, and "Culture Supernatant" denotes PVDF membranes blotted from those gels on which culture supernatants from individual cells were electrophoresed.

The expression vector pTB2116 obtained in Example 1 comprising the cDNA having the base sequence as shown in SEQ ID NO: 9 was transiently transfected into COS7 cells using a transfection reagent TransFast (Promega). Subsequently, the cells were transferred to a serum-free medium to allow them to produce a polypeptide (partial fragment III) having the amino acid sequence as shown in SEQ ID NO: 10 in the serum-free medium. With respect to partial fragments I, II, IV and V, corresponding expression vectors were separately transfected into COS7 cells in the same manner to allow the resultant cells to produce respective fragments in the serum-free medium. In order to confirm expression, an aliquot of each culture supernatant was subjected to SDS-PAGE (12.5% gel) under non-reducing conditions. After the gel was transferred onto a PVDF membrane by a semi-dry method, the fragment of interest was detected by Western blotting using anti-Myc monoclonal antibody 9E10 (Sigma). As shown in FIG. 3, it was confirmed that overlapping partial fragments I to V of human cubilin were expressed in COS7 cells and secreted into the culture supernatant.

Example 3

Figure 4:
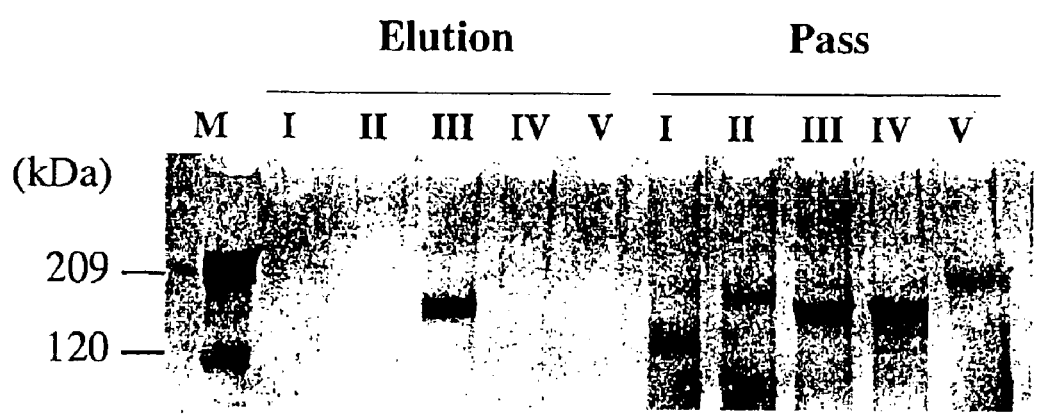
FIG. 4 shows the results of Western blotting carried out in Example 3. In this Figure, lanes I to V show culture supernatants containing partial fragments I to V, respectively, and lane M shows molecular markers. "Elution" denotes PVDF membranes blotted from those gels on which EDTA-selectively eluted fractions were electrophoresed, and "Pass" denotes PVDF membranes blotted from those gels on which non-binding fractions were electrophoresed.

Interaction between Human Apolipoprotein A-I-Conjugated Resin and Partial Fragments of Human Cubilin Human apolipoprotein A-I-cross linking Sepharose resin was prepared by mixing human apolipoprotein A-I (Sigma) and swollen CNBr-activated Sepharose (Amersham Pharmacia) at a ratio of 2 mg/1 ml in a binding buffer (pH 8.3) containing 0.5 M NaCl and 0.1 M NaHCO$_3$ overnight at 4° C. The resultant human apolipoprotein A-I-linking resin (50 μl) was mixed with 200 μl each of the culture supernatants obtained in Example 2 containing partial fragments I to V, respectively, overnight at 4° C. After removal of the unbound fraction by centrifugation, the reaction mixture was washed with 400 μl of 0.2% bovine albumin-containing D-MEM medium (Gibco) four times, with D-MEM medium once, and mixed with 20 mM EDTA-containing D-MEM medium. After incubation for 5 min, a fraction that elutes in an EDTA selective manner was obtained by centrifugation. The unbound fraction and the fraction that elutes in an EDTA selective manner were subjected to SDS-PAGE (12.5% gel) separately. The resultant gel was transferred onto a PVDF membrane by a semi-dry method and subjected to detection using anti-Myc monoclonal antibody 9E10 (Sigma). As shown in FIG. 4, it was revealed that only partial fragment III bound to the human apolipoprotein A-I-linking resin and was eluted with EDTA selectively.

From the above, it was made clear that the human apolipoprotein A-I-binding site of human cubilin is in partial fragment III (corresponding to the fragment peptide CUB7–CUB14).

Example 4

The Apo A-I-Binding Action of CUB9–CUB 14 Fragment Peptide

In order to further specify the location of the human apolipoprotein A-I-binding site, a cDNA encoding the amino acid sequence as shown in SEQ ID NO: 19 corresponding to fragment peptide CUB9–CUB14 [having the amino acid sequence consisting of the amino acids from position 1391 to position 2091 of the amino acid sequence of human cubilin mature protein (FIGS. 1 and 2)] and a cDNA encoding the amino acid sequence as shown in SEQ ID NO:

20 corresponding to fragment peptide CUB7–CUB12 were sub-cloned separately into the expression vector used in Example 1.

The above-mentioned cDNA (SEQ ID NO: 22) encoding human CUB9–CUB14 fragment peptide was inserted into pSecTag2 vector. The resultant plasmid pTB2231 was introduced into *Escherichia coli* DH5α by a publicly known method to obtain a transformant designated *Escherichia coli* DH5α/pTB2231.

These cubilin partial fragments were expressed in culture supernatant of COS7 cells in the same manner as in Example 2, and their interaction with human apolipoprotein A-I-inking resin was examined in the same manner as in Example 3.

Figure 5:
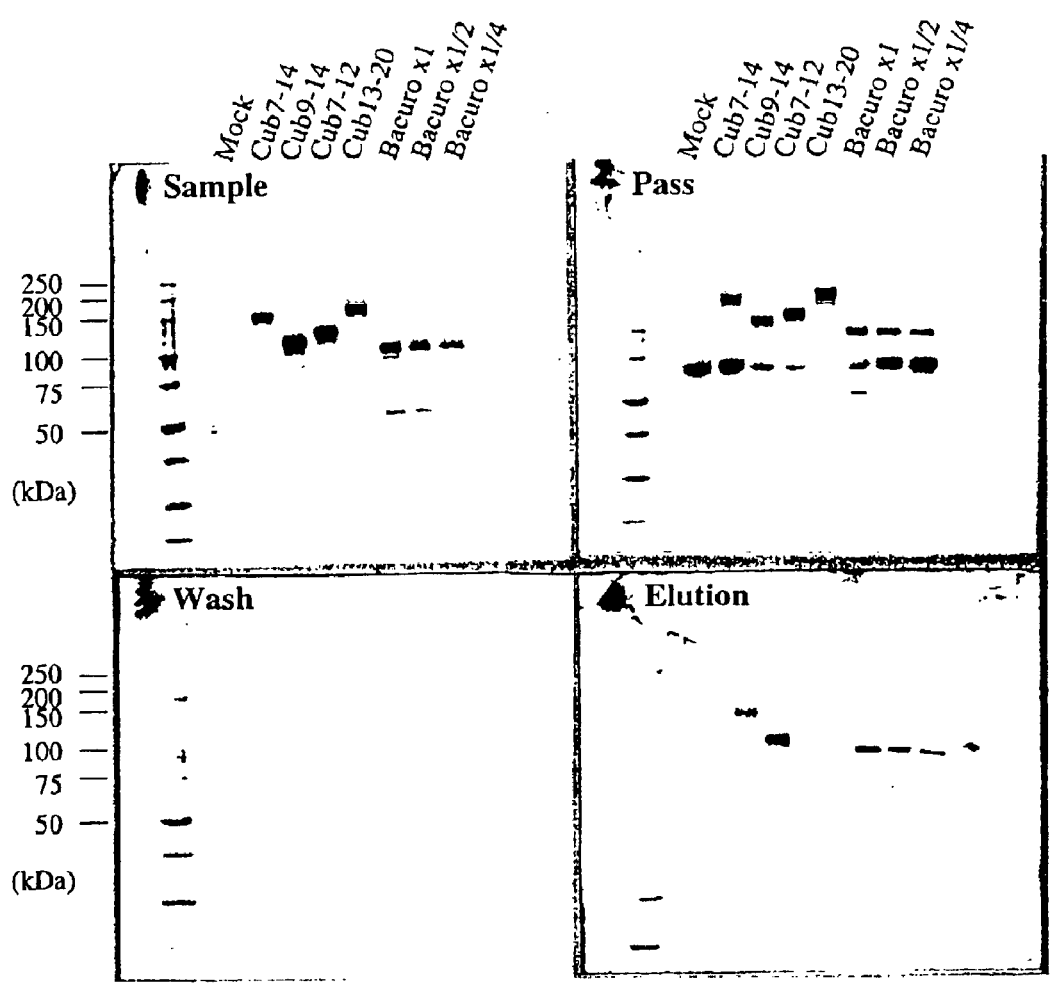
FIG. 5 shows the results of Western blotting carried out in Examples 4 and 5.

The partial protein containing CUB9–CUB14 fragment peptide bound to human apolipoprotein A-I-linking resin (FIG. 5). This result revealed that the human apolipoprotein A-I-binding site of human cubilin is in CUB9–CUB 14 fragment peptide.

Example 5

The Apo A-I-Binding Action of CUB9–CUB 14 Fragment Peptide

The cDNA (SEQ ID NO: 22) encoding CUB9–CUB14 fragment peptide was inserted into a baculovirus for expressing the peptide in insect cells.

Specifically, a cDNA encoding the amino acid sequence as shown in SEQ ID NO: 21 (Myc tag and His tag are added to the C-terminal of CUB9–CUB14 fragment peptide) was sub-cloned into pFasBac vector. Using this vector, a baculovirus was constructed according to conventional methods to thereby prepare a system for expressing the fragment peptide in culture supernatant of HiFive cell, an insect cell.

It was found in the same manner as in Example 4 that the partial protein having CUB9–CUB14 fragment peptide expressed in the culture supernatant bound to human apolipoprotein A-I-linking resin (FIG. 5). This result revealed that CUB9–CUB14 fragment peptide expressed in an insect cell also binds to human apolipoprotein A-I.

Example 6

Purification of CUB9–CUB14 Fragment Peptide

The CUB9–CUB14 fragment peptide expressed in the insect cell obtained in Example 5 was purified using the His tag added to the C-terminal.

Specifically, the culture supernatant was precipitated with 50% saturated ammonium sulfate, and the precipitate was recovered by centrifugation (12,000 g, 30 min). The resultant precipitate was dissolved in a buffer containing 20 mM Tris-HCl (pH 7.4), 500 mM NaCl, 10 mM imidazole and 0.1% sodium azide. The resultant solution was applied to HiTrap Chelating column (Amersham Pharmacia), charged with 0.1 M $NiSO_4$ and equilibrated with the same buffer. After washing with the same buffer, a linear gradient from 10 mM imidazole to 200 mM imidazole was formed with the buffer to thereby elute CUB9–CUB14 fragment peptide.

The thus eluted fractions were subjected to SDS-PAGE (12.5% gel). The resultant gels stained with CBB are shown in FIG. 6A. The gels transferred onto PVDF membrane and subjected to detection with anti-Myc monoclonal antibody 9E10 (Sigma) are shown in FIG. 6B.

From these results, it was found that the eluted fractions contain CUB9–CUB14 fragment peptide as a major component.

Example 7

Quantitative Determination of the Binding Between CUB9–CUB14 Fragment Peptide and Apo A-I The CUB9–CUB14 fragment peptide expressed in the insect cell obtained in Example 5 was dissolved in a buffer containing 20 mM Tris-HCl, 500 mM NaCl, 2 mM $CaCl_2$ and 0.1% sodium azide to give a final concentration of 1–5 μg/ml, and incubated in a fluoroimmunoassay plate (Clini plate Black enhanced binding; Flow Lab.) containing 100 μl /well of this solution to thereby solidify the peptide. After blocking the non-specific binding sites with 200 μl/well of SuperBlock TBS (Pierce), the peptide was incubated with biotin-added human apolipoprotein A-I and, after washing, reacted with streptavidin β-galactosidase. After washing, β-galactosidase activity was measured by conventional methods to thereby quantitatively determine the binding between solidified CUB9–CUB14 fragment peptide and human apolipoprotein A-I. For the above binding reaction and washing, a buffer containing 20 mM Tris-HCl (pH 7.4), 150 mM NaCl, 1 mM $CaCl_2$, 0.1% sodium azide and 5% (v/v) Block-Ace (Dainippon Pharmaceutical Co., Ltd.) was used.

As shown in FIG. 7, binding reaction dependent on the amount of solidified CUB9–CUB14 fragment peptide and dependent on the amount of biotin-added human apolipoprotein A-I was recognized. The binding was so strong that the amount of binding did not change even after washing for 2–3 hours. From the binding curve, the approximate affinity (Kd) of apolipoprotein A-I is judged to be at levels of 20–100 nM.

Example 8

Screening Method

The CUB9–CUB14 fragment peptide expressed in the insect cell obtained in Example 5 was incubated at a concentration of 3 μg/ml in a fluoroimmunoassay plate (Clini plate Black enhanced binding; Flow Lab.) containing 100 μl/well of the peptide solution to thereby solidify the peptide. After blocking the non-specific binding sites with 200 μl/well of SuperBlock TBS (Pierce), the test compound was incubated with biotin-added human apolipoprotein A-I (final concentration: 0.1 μg/ml) overnight. After washing, the test compound (100 μl/well) was reacted with 0.05 U/ml of streptavidin β-galactosidase for 1 hour. After washing, 0.5 mM 4-methylumbelliferyl β-D-galactopyranoside was added to the reaction solution dissolved in a buffer containing 10 mM $K_2HPO_4$, 150 nM NaCl, 2 mM $MgCl_2$, 0.1% sodium azide and 0.2% BSA (pH 7.0) and incubated, followed by measurement of excitation at 365 nm and absorbance at 460 nm. For the above binding reaction and washing, a buffer containing 20 mM Tris-HCl (pH 7.4), 150 mM NaCl, 1 mM $CaCl_2$, 0.1% sodium azide and 5% (v/v) Block-Ace (Dainippon Pharmaceutical Co., Ltd.) was used.

INDUSTRIAL APPLICABILITY

The polypeptide of the invention (or amide or ester thereof, or salts thereof) and the DNA of the invention may be used as medicines such as therapeutic and/or prophylactic agent for diabetes, obesity, arteriosclerosis, hyperlipemia, hypertriglyceridemia, hypo-high density lipoproteinemia, hypoapolipoproteinemia A-I, or nervousl disorders.

Further, compounds or salts thereof, which are obtainable by a screening method or kit using the polypeptide of the invention, that inhibit the binding of cubilin to apolipoprotein A-I may be used as medicines such as therapeutics and/or prophylactics for diseases such as hyperlipemia, hypertriglyceridemia, hypo-high density lipoproteinemia, hypoapolipoproteinemia A-I, after meal hyperlipemia, diabetes, obesity, arteriosclerosis, myocardial infarction or angina; and compounds or salts thereof, which are obtainable by a screening method or kit using the polypeptide of the invention, that promote the binding of cubilin to apolipoprotein A-I may be used as medicines such as therapeutics and/or prophylactics for diseases such as renal disorders, nephritis, nephropathy, proteinuria, neurological disorders or vitamin $B_{12}$ deficiency.

Further, since the antibody of the invention can specifically recognize the polypeptide of the invention and cubilin, it may be used in quantitative determination of the polypeptide of the invention in a sample solution. Also, the antibody of the invention may be used as a medicine such as a therapeutic and/or prophylactic agent for diseases caused by excessive expression of the polypeptide of the invention.

The DNA of the invention may be useful as a gene diagnostic agent when used as a probe, for example.

What is claimed is:

1. An isolated polypeptide, amide or ester thereof, or salt thereof consisting of the amino acid sequence of SEQ ID NO: 19.

2. A pharmaceutical composition comprising the isolated polypeptide, amide or ester thereof, or salt thereof of claim 1 and a pharmaceutically acceptable carrier, excipient or diluent.

* * * * *

SEQUENCE LISTING

<160> NUMBER OF SEQ ID NOS: 22

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
tgcgggggta atctcaccac ttc                                          23

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ctgcagttct gattgtttgg ataa                                         24

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
tatccaaaca atcagaactg ca                                           22

<210> SEQ ID NO 4
<211> LENGTH: 25
<212> TYPE: DNA
<213> ORGANISM: Artificial Sequence
<220> FEATURE:
<223> OTHER INFORMATION: primer

<400> SEQUENCE: 4
gctcttgtga aaggatgcat tgaag                                        25

<210> SEQ ID NO 5
<211> LENGTH: 1451
<212> TYPE: DNA
<213> ORGANISM: Human

<400> SEQUENCE: 5
tgcgggggta atctcaccac ttcaagcggc acgttcatat ctcccaacta cccgatgccc      60
tattaccaca gctctgaatg ctactggtgg ttgaaatcta gccacggcag cgcatttgaa     120

```
ctggaattca aagactttca cttggagcat catccaaact gcactttaga ttacctggct      180
gtatatgatg gcccaagtag caactctcat ctgctaactc agctttgtgg ggatgagaaa      240
ccccctctta ttcgttctag tggagacagc atgtttataa aactgaggac agatgaaggt      300
cagcaaggac gtggcttcaa ggctgaatac cggcagacat gtgagaatgt ggtaatagtc      360
aatcaaacct atggcatctt agagagtata gggtatccga atccttattc tgaaaatcag      420
cattgcaact ggaccatccg ggcaacaaca gcaacactg tgaactacac attttagca      480 tttgacttgg aacatcacat aaactgctcc acagattatt tagagctcta tgatggacca      540
cggcagatgg gacgctactg tggagtagac ctgcccctc cagggagtac tacaagctcc      600
aagcttcaag tgctgctcct tacagatggg gttggccgcc gtgagaaagg atttcagatg      660
cagtggtttg tttacggttg tggtggagag ctgtctgggg ccacaggctc cttcagcagc      720
cccgggttcc ccaacaggta tccaccaaac aaggagtgta tctggtacat taggacggac      780
cccgggagta gcattcagct caccatccat gacttcgatg tggagtatca ttcaaggtgc      840
aactttgatg tcttggagat ctatggaggc cccgatttcc actctcccag aatagcccaa      900
ctgtgtaccc agagatcacc tgagaacccc atgcaggtct ccagcactgg aaatgagcta      960
gcaattcgat tcaagaccga cttgtccata aatgggagag gcttcaatgc gtcatggcaa     1020
gcagtcactg gaggttgtgg tgggattttc caggctccca gtggagagat acattctcca     1080
aattacccca gtccttatag gagcaacaca gactgttctt gggtcattcg ggttgacaga     1140
aatcatcgtg ttctcttgaa cttcactgac tttgatcttg aatcacaaga ctcttgtatt     1200
atggcatacg atggcttaag ctccacaatg tcccgccttg ccaggacgtg tggaagggag     1260
cagctggcta accccatcgt ctcctcagga aacagcctct tcttgagatt tcagtctggc     1320
ccttccagac agaacagagg cttccgagct caattcaggc aagcctgcgg aggccacatc     1380
ctcaccagct catttgatac tgtttcctct ccacggttcc ctgccaatta tccaaacaat     1440
cagaactgca g                                                          1451
```

<210> SEQ ID NO 6
<211> LENGTH: 1353
<212> TYPE: DNA
<213> ORGANISM: Human

<400> SEQUENCE: 6

```
tatccaaaca atcagaactg cagctggatc attcaagcgc aacctccatt aaatcatatc       60
accctctctt ttacccactt tgaacttgaa agaagcacaa cgtgtgcacg tgactttgta      120
gaaattttgg atggcggcca cgaagacgcg cccctccgag gccgttactg tggcaccgac      180
atgccccatc ctatcacatc cttcagcagc gccctgacgc tgagattcgt ctctgattct      240
agcatcagtg ctgggggttt ccacaccacg gtcaccgcat cagtgtcggc ttgtggtgga      300
acgttctaca tggctgaagg catcttcaac agccctggct acccagacat ttatccccct      360
aatgtggaat gtgtctggaa catcgtcagt tcccctggca accggctcca gctgtcttt      420 atatctttcc agttggaaga ctctcaggac tgcagcagag attttgtgga gatccgtgaa      480
ggaaatgcca cgggtcactt ggtgggacga tactgtggaa actccttccc tctcaattat      540
tcttccatcg ttggacatac cctgtgggtc agatttatct cagatggttc tggcagcggc      600
acgggcttcc aggccacatt tatgaagata tttggcaatg ataatattgt gggaactcat      660
gggaaagtcg cctctccttt ctggcctgaa aactacccac ataactccaa ttaccaatgg      720
```

```
acagtaaatg tgaatgcatc tcacgttgtc catggtagaa tcttggagat ggacatagaa      780
gaaatacaaa actgctatta tgacaaatta aggatctatg atgggcctag cattcacgcc      840
cgcctaattg gagcttactg tggtacccag actgaatctt tcagctccac tggaaattct      900
ttgacatttc atttttactc cgactcttca atctcaggga agggattcct tctggagtgg      960
tttgcagtgg atgcacctga tggtgtttta cctaccattg ctccaggtgc ttgtggtggc     1020
ttcctgagga cgggagatgc acccgtgttt ctcttctccc cgggctggcc tgacagttac     1080
agtaatagag tggactgtac gtggctcatc caggctcccg actctaccgt ggaactcaac     1140
attctttccc tggacattga atctcaccga acgtgtgcct atgatagcct tgtgatacga     1200
gatggagata taacttggcc cagcagcta gcagttctct gtggcagaga tccctggg       1260 cccatccggt ctactggaga gtacatgttc atccgcttca cctcggactc cagtgtaacc     1320
agggcaggct tcaatgcatc ctttcacaag agc                                  1353

<210> SEQ ID NO 7
<211> LENGTH: 28
<212> TYPE: DNA
<213> ORGANISM: Artificial Sequence
<220> FEATURE:
<223> OTHER INFORMATION: primer

<400> SEQUENCE: 7
cgggatcccg tgcgggggta atctcacc                                          28

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
tatgcggccg catagctctt gtgaaaggat gcatt                                  35

<210> SEQ ID NO 9
<211> LENGTH: 2781
<212> TYPE: DNA
<213> ORGANISM: Human

<400> SEQUENCE: 9
tgcgggggta atctcaccac ttcaagcggc acgttcatat ctcccaacta cccgatgccc       60
tattaccaca gctctgaatg ctactggtgg ttgaaatcta gccacggcag cgcatttgaa      120
ctggaattca aagctttca cttggagcat catccaaact gcactttaga ttacctggct      180
gtatatgatg gcccaagtag caactctcat ctgctaactc agctttgtgg ggatgagaaa      240 cccctctta ttcgttctag tggagacagc atgtttataa aactgaggac agatgaaggt      300
cagcaaggac gtgcttcaa ggctgaatac cggcagacat gtgagaatgt ggtaatagtc      360
aatcaaacct atggcatctt agagagtata gggtatccga atccttattc tgaaaatcag      420
cattgcaact ggaccatccg ggcaacaaca ggcaacactg tgaactacac atttttagca      480
tttgacttgg aacatcacat aaactgctcc acagattatt tagagctcta tgatggacca      540
cggcagatgg gacgctactg tggagtagac ctgcccccta cagggagtac tacaagctcc      600
aagcttcaag tgctgctcct tacagatggg gttggccgcc gtgagaaagg atttcagatg      660
cagtggtttg tttacggttg tggtggagag ctgtctgggg ccacaggctc cttcagcagc      720
cccgggttcc ccaacaggta tccaccaaac aaggagtgta tctggtacat taggacggac      780
```

-continued

| | |
|---|---|
| cccgggagta gcattcagct caccatccat gacttcgatg tggagtatca ttcaaggtgc | 840 |
| aactttgatg tcttggagat ctatggaggc cccgatttcc actctcccag aatagcccaa | 900 |
| ctgtgtaccc agagatcacc tgagaacccc atgcaggtct ccagcactgg aaatgagcta | 960 |
| gcaattcgat tcaagaccga cttgtccata aatgggagag gcttcaatgc gtcatggcaa | 1020 |
| gcagtcactg gaggttgtgg tgggattttc caggctccca gtggagagat acattctcca | 1080 |
| aattacccca gtccttatag gagcaacaca gactgttctt gggtcattcg ggttgacaga | 1140 |
| aatcatcgtt ttctcttgaa cttcactgac tttgatcttg aatcacaaga ctcttgtatt | 1200 |
| atggcatacg atggcttaag ctccacaatg tcccgccttg ccaggacgtg tggaagggag | 1260 |
| cagctggcta cccccatcgt ctcctcagga acagcctct tcttgagatt tcagtctggc | 1320 |
| ccttccagac agaacagagg cttccgagct caattcaggc aagcctgcgg aggccacatc | 1380 |
| ctcaccagct catttgatac tgtttcctct ccacggttcc ctgccaatta tccaaacaat | 1440 |
| cagaactgca gctggatcat tcaagcgcaa cctccattaa atcatatcac cctctctttt | 1500 |
| acccactttg aacttgaaag aagcacaacg tgtgcacgtg actttgtaga aattttggat | 1560 |
| ggcggccacg aagacgcgcc cctccgaggc cgttactgtg gcaccgacat gccccatcct | 1620 |
| atcacatcct tcagcagcgc cctgacgctg agattcgtct ctgattctag catcagtgct | 1680 |
| gggggttttc acaccacggt caccgcatca gtgtcggctt gtggtggaac gttctacatg | 1740 |
| gctgaaggca tcttcaacag ccctggctac ccagacattt atcccctaa tgtggaatgt | 1800 |
| gtctggaaca tcgtcagttc ccctggcaac cggctccagc tgtcttttat atctttccag | 1860 |
| ttggaagact ctcaggactg cagcagagat tttgtggaga tccgtgaagg aaatgccacg | 1920 |
| ggtcacttgg tgggacgata ctgtggaaac tccttccctc tcaattattc ttccatcgtt | 1980 |
| ggacataccc tgtgggtcag atttatctca gatggttctg gcagcggcac gggcttccag | 2040 |
| gccacattta tgaagatatt tggcaatgat aatattgtgg gaactcatgg gaaagtcgcc | 2100 |
| tctcctttct ggcctgaaaa ctacccacat aactccaatt accaatggac agtaaatgtg | 2160 |
| aatgcatctc acgttgtcca tggtagaatc ttggagatgg acatagaaga aatacaaaac | 2220 |
| tgctattatg acaaattaag gatctatgat gggcctagca ttcacgcccg cctaattgga | 2280 |
| gcttactgtg gtacccagac tgaatctttc agctccactg gaaattcttt gacatttcat | 2340 |
| ttttactccg actcttcaat ctcagggaag ggattccttc tggagtggtt tgcagtggat | 2400 |
| gcacctgatg gtgttttacc taccattgct ccaggtgctt gtggtggctt cctgaggacg | 2460 |
| ggagatgcac ccgtgtttct cttctccccg ggctggcctg acagttacag taatagagtg | 2520 |
| gactgtacgt ggctcatcca ggctcccgac tctaccgtgg aactcaacat tctttccctg | 2580 |
| gacattgaat ctcaccgaac gtgtgcctat gatagccttg tgatacgaga tggagataat | 2640 |
| aacttggccc agcagctagc agttctctgt ggcagagaga tccctgggcc catccggtct | 2700 |
| actggagagt acatgttcat ccgcttcacc tcggactcca gtgtaaccag ggcaggcttc | 2760 |
| aatgcatcct ttcacaagag c | 2781 |

<210> SEQ ID NO 10
<211> LENGTH: 927
<212> TYPE: PRT
<213> ORGANISM: Human

<400> SEQUENCE: 10

Cys Gly Gly Asn Leu Thr Thr Ser Ser Gly Thr Phe Ile Ser Pro Asn
 　　　　　　　　 5　　　　　　　　　　　10　　　　　　　　　　　15

```
Tyr Pro Met Pro Tyr Tyr His Ser Ser Glu Cys Tyr Trp Trp Leu Lys
            20                  25                  30

Ser Ser His Gly Ser Ala Phe Glu Leu Glu Phe Lys Asp Phe His Leu
        35                  40                  45

Glu His His Pro Asn Cys Thr Leu Asp Tyr Leu Ala Val Tyr Asp Gly
        50                  55                  60

Pro Ser Ser Asn Ser His Leu Leu Thr Gln Leu Cys Gly Asp Glu Lys
65                  70                  75                  80

Pro Pro Leu Ile Arg Ser Ser Gly Asp Ser Met Phe Ile Lys Leu Arg
                85                  90                  95

Thr Asp Glu Gly Gln Gln Gly Arg Gly Phe Lys Ala Glu Tyr Arg Gln
            100                 105                 110

Thr Cys Glu Asn Val Val Ile Val Asn Gln Thr Tyr Gly Ile Leu Glu
            115                 120                 125

Ser Ile Gly Tyr Pro Asn Pro Tyr Ser Glu Asn Gln His Cys Asn Trp
130                 135                 140

Thr Ile Arg Ala Thr Thr Gly Asn Thr Val Asn Tyr Thr Phe Leu Ala
145                 150                 155                 160

Phe Asp Leu Glu His His Ile Asn Cys Ser Thr Asp Tyr Leu Glu Leu
                165                 170                 175

Tyr Asp Gly Pro Arg Gln Met Gly Arg Tyr Cys Gly Val Asp Leu Pro
            180                 185                 190

Pro Pro Gly Ser Thr Thr Ser Ser Lys Leu Gln Val Leu Leu Leu Thr
            195                 200                 205

Asp Gly Val Gly Arg Arg Glu Lys Gly Phe Gln Met Gln Trp Phe Val
210                 215                 220

Tyr Gly Cys Gly Gly Glu Leu Ser Gly Ala Thr Gly Ser Phe Ser Ser
225                 230                 235                 240

Pro Gly Phe Pro Asn Arg Tyr Pro Pro Asn Lys Glu Cys Ile Trp Tyr
                245                 250                 255

Ile Arg Thr Asp Pro Gly Ser Ser Ile Gln Leu Thr Ile His Asp Phe
            260                 265                 270

Asp Val Glu Tyr His Ser Arg Cys Asn Phe Asp Val Leu Glu Ile Tyr
            275                 280                 285

Gly Gly Pro Asp Phe His Ser Pro Arg Ile Ala Gln Leu Cys Thr Gln
290                 295                 300

Arg Ser Pro Glu Asn Pro Met Gln Val Ser Ser Thr Gly Asn Glu Leu
305                 310                 315                 320

Ala Ile Arg Phe Lys Thr Asp Leu Ser Ile Asn Gly Arg Gly Phe Asn
                325                 330                 335

Ala Ser Trp Gln Ala Val Thr Gly Gly Cys Gly Gly Ile Phe Gln Ala
            340                 345                 350

Pro Ser Gly Glu Ile His Ser Pro Asn Tyr Pro Ser Pro Tyr Arg Ser
            355                 360                 365

Asn Thr Asp Cys Ser Trp Val Ile Arg Val Asp Arg Asn His Arg Val
370                 375                 380

Leu Leu Asn Phe Thr Asp Phe Asp Leu Glu Ser Gln Asp Ser Cys Ile
385                 390                 395                 400

Met Ala Tyr Asp Gly Leu Ser Ser Thr Met Ser Arg Leu Ala Arg Thr
                405                 410                 415

Cys Gly Arg Glu Gln Leu Ala Asn Pro Ile Val Ser Ser Gly Asn Ser
            420                 425                 430
```

-continued

```
Leu Phe Leu Arg Phe Gln Ser Gly Pro Ser Arg Gln Asn Arg Gly Phe
        435                 440                 445

Arg Ala Gln Phe Arg Gln Ala Cys Gly Gly His Ile Leu Thr Ser Ser
        450                 455                 460

Phe Asp Thr Val Ser Ser Pro Arg Phe Pro Ala Asn Tyr Pro Asn Asn
465                 470                 475                 480

Gln Asn Cys Ser Trp Ile Ile Gln Ala Gln Pro Pro Leu Asn His Ile
                485                 490                 495

Thr Leu Ser Phe Thr His Phe Glu Leu Glu Arg Ser Thr Thr Cys Ala
                500                 505                 510

Arg Asp Phe Val Glu Ile Leu Asp Gly His Glu Asp Ala Pro Leu
        515                 520                 525

Arg Gly Arg Tyr Cys Gly Thr Asp Met Pro His Pro Ile Thr Ser Phe
        530                 535                 540

Ser Ser Ala Leu Thr Leu Arg Phe Val Ser Asp Ser Ser Ile Ser Ala
545                 550                 555                 560

Gly Gly Phe His Thr Thr Val Thr Ala Ser Val Ser Ala Cys Gly Gly
                565                 570                 575

Thr Phe Tyr Met Ala Glu Gly Ile Phe Asn Ser Pro Gly Tyr Pro Asp
                580                 585                 590

Ile Tyr Pro Pro Asn Val Glu Cys Val Trp Asn Ile Val Ser Ser Pro
        595                 600                 605

Gly Asn Arg Leu Gln Leu Ser Phe Ile Ser Phe Gln Leu Glu Asp Ser
        610                 615                 620

Gln Asp Cys Ser Arg Asp Phe Val Glu Ile Arg Glu Gly Asn Ala Thr
625                 630                 635                 640

Gly His Leu Val Gly Arg Tyr Cys Gly Asn Ser Phe Pro Leu Asn Tyr
                645                 650                 655

Ser Ser Ile Val Gly His Thr Leu Trp Val Arg Phe Ile Ser Asp Gly
                660                 665                 670

Ser Gly Ser Gly Thr Gly Phe Gln Ala Thr Phe Met Lys Ile Phe Gly
        675                 680                 685

Asn Asp Asn Ile Val Gly Thr His Gly Lys Val Ala Ser Pro Phe Trp
        690                 695                 700

Pro Glu Asn Tyr Pro His Asn Ser Asn Tyr Gln Trp Thr Val Asn Val
705                 710                 715                 720

Asn Ala Ser His Val Val His Gly Arg Ile Leu Glu Met Asp Ile Glu
                725                 730                 735

Glu Ile Gln Asn Cys Tyr Tyr Asp Lys Leu Arg Ile Tyr Asp Gly Pro
                740                 745                 750

Ser Ile His Ala Arg Leu Ile Gly Ala Tyr Cys Gly Thr Gln Thr Glu
        755                 760                 765

Ser Phe Ser Ser Thr Gly Asn Ser Leu Thr Phe His Phe Tyr Ser Asp
        770                 775                 780

Ser Ser Ile Ser Gly Lys Gly Phe Leu Leu Glu Trp Phe Ala Val Asp
785                 790                 795                 800

Ala Pro Asp Gly Val Leu Pro Thr Ile Ala Pro Gly Ala Cys Gly Gly
                805                 810                 815

Phe Leu Arg Thr Gly Asp Ala Pro Val Phe Leu Phe Ser Pro Gly Trp
        820                 825                 830

Pro Asp Ser Tyr Ser Asn Arg Val Asp Cys Thr Trp Leu Ile Gln Ala
        835                 840                 845

Pro Asp Ser Thr Val Glu Leu Asn Ile Leu Ser Leu Asp Ile Glu Ser
```

-continued

```
                850                 855                 860
His Arg Thr Cys Ala Tyr Asp Ser Leu Val Ile Arg Asp Gly Asp Asn
865                 870                 875                 880

Asn Leu Ala Gln Gln Leu Ala Val Leu Cys Gly Arg Glu Ile Pro Gly
                885                 890                 895

Pro Ile Arg Ser Thr Gly Glu Tyr Met Phe Ile Arg Phe Thr Ser Asp
                900                 905                 910

Ser Ser Val Thr Arg Ala Gly Phe Asn Ala Ser Phe His Lys Ser
                915                 920                 925

<210> SEQ ID NO 11
<211> LENGTH: 27
<212> TYPE: DNA
<213> ORGANISM: Artificial Sequence
<220> FEATURE:
<223> OTHER INFORMATION: primer

<400> SEQUENCE: 11
ggcgcgcccg tggagaactt gagctgc                                   27

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
tatgcggccg cataagcgac ttgataaaca gctct                          35

<210> SEQ ID NO 13
<211> LENGTH: 34
<212> TYPE: DNA
<213> ORGANISM: Artificial Sequence
<220> FEATURE:
<223> OTHER INFORMATION: primer

<400> SEQUENCE: 13
ggggtacccc tgtggagagt gggtctcttc caaa                           34

<210> SEQ ID NO 14
<211> LENGTH: 30
<212> TYPE: DNA
<213> ORGANISM: Artificial Sequence
<220> FEATURE:
<223> OTHER INFORMATION: primer

<400> SEQUENCE: 14
cggatcccga ccgtaaacaa accactgcat                                30

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15
tgcactgcag tgcaaatgat aatattgtgg gaactca                        37

<210> SEQ ID NO 16
<211> LENGTH: 37
<212> TYPE: DNA
<213> ORGANISM: Artificial Sequence
```

```
<220> FEATURE:
<223> OTHER INFORMATION: primer

<400> SEQUENCE: 16
tttgcggccg caaaacctaa agtttgtgtg ttccacg                                37

<210> SEQ ID NO 17
<211> LENGTH: 37
<212> TYPE: DNA
<213> ORGANISM: Artificial Sequence
<220> FEATURE:
<223> OTHER INFORMATION: primer

<400> SEQUENCE: 17
ggggtacccc tgtggtgggt ctcttccaaa tactcct                                37

<210> SEQ ID NO 18
<211> LENGTH: 37
<212> TYPE: DNA
<213> ORGANISM: Artificial Sequence
<220> FEATURE:
<223> OTHER INFORMATION: primer

<400> SEQUENCE: 18
cgggatcccg gctgtcccaa gttaatcgga atgcgga                                37

<210> SEQ ID NO 19
<211> LENGTH: 701
<212> TYPE: PRT
<213> ORGANISM: Human

<400> SEQUENCE: 19
```

Cys Gly Gly Glu Leu Ser Gly Ala Thr Gly Ser Phe Ser Ser Pro Gly
              5                  10                  15

Phe Pro Asn Arg Tyr Pro Pro Asn Lys Glu Cys Ile Trp Tyr Ile Arg
             20                  25                  30

Thr Asp Pro Gly Ser Ser Ile Gln Leu Thr Ile His Asp Phe Asp Val
         35                  40                  45

Glu Tyr His Ser Arg Cys Asn Phe Asp Val Leu Glu Ile Tyr Gly Gly
     50                  55                  60

Pro Asp Phe His Ser Pro Arg Ile Ala Gln Leu Cys Thr Gln Arg Ser
 65                  70                  75                  80

Pro Glu Asn Pro Met Gln Val Ser Ser Thr Gly Asn Glu Leu Ala Ile
                 85                  90                  95

Arg Phe Lys Thr Asp Leu Ser Ile Asn Gly Arg Gly Phe Asn Ala Ser
            100                 105                 110

Trp Gln Ala Val Thr Gly Gly Cys Gly Gly Ile Phe Gln Ala Pro Ser
        115                 120                 125

Gly Glu Ile His Ser Pro Asn Tyr Pro Ser Pro Tyr Arg Ser Asn Thr
    130                 135                 140

Asp Cys Ser Trp Val Ile Arg Val Asp Arg Asn His Arg Val Leu Leu
145                 150                 155                 160

Asn Phe Thr Asp Phe Asp Leu Glu Ser Gln Asp Ser Cys Ile Met Ala
                165                 170                 175

Tyr Asp Gly Leu Ser Ser Thr Met Ser Arg Leu Ala Arg Thr Cys Gly
            180                 185                 190

Arg Glu Gln Leu Ala Asn Pro Ile Val Ser Ser Gly Asn Ser Leu Phe
        195                 200                 205

Leu Arg Phe Gln Ser Gly Pro Ser Arg Gln Asn Arg Gly Phe Arg Ala

```
                210                 215                 220
Gln Phe Arg Gln Ala Cys Gly Gly His Ile Leu Thr Ser Ser Phe Asp
225                 230                 235                 240

Thr Val Ser Ser Pro Arg Phe Pro Ala Asn Tyr Pro Asn Asn Gln Asn
            245                 250                 255

Cys Ser Trp Ile Ile Gln Ala Gln Pro Pro Leu Asn His Ile Thr Leu
            260                 265                 270

Ser Phe Thr His Phe Glu Leu Glu Arg Ser Thr Thr Cys Ala Arg Asp
            275                 280                 285

Phe Val Glu Ile Leu Asp Gly Gly His Glu Asp Ala Pro Leu Arg Gly
            290                 295                 300

Arg Tyr Cys Gly Thr Asp Met Pro His Pro Ile Thr Ser Phe Ser Ser
305                 310                 315                 320

Ala Leu Thr Leu Arg Phe Val Ser Asp Ser Ser Ile Ser Ala Gly Gly
            325                 330                 335

Phe His Thr Thr Val Thr Ala Ser Ser Ala Cys Gly Gly Thr Phe
            340                 345                 350

Tyr Met Ala Glu Gly Ile Phe Asn Ser Pro Gly Tyr Pro Asp Ile Tyr
            355                 360                 365

Pro Pro Asn Val Glu Cys Val Trp Asn Ile Val Ser Ser Pro Gly Asn
            370                 375                 380

Arg Leu Gln Leu Ser Phe Ile Ser Phe Gln Leu Glu Asp Ser Gln Asp
385                 390                 395                 400

Cys Ser Arg Asp Phe Val Glu Ile Arg Glu Gly Asn Ala Thr Gly His
            405                 410                 415

Leu Val Gly Arg Tyr Cys Gly Asn Ser Phe Pro Leu Asn Tyr Ser Ser
            420                 425                 430

Ile Val Gly His Thr Leu Trp Val Arg Phe Ile Ser Asp Gly Ser Gly
            435                 440                 445

Ser Gly Thr Gly Phe Gln Ala Thr Phe Met Lys Ile Phe Gly Asn Asp
            450                 455                 460

Asn Ile Val Gly Thr His Gly Lys Val Ala Ser Pro Phe Trp Pro Glu
465                 470                 475                 480

Asn Tyr Pro His Asn Ser Asn Tyr Gln Trp Thr Val Asn Val Asn Ala
            485                 490                 495

Ser His Val Val His Gly Arg Ile Leu Glu Met Asp Ile Glu Glu Ile
            500                 505                 510

Gln Asn Cys Tyr Tyr Asp Lys Leu Arg Ile Tyr Asp Gly Pro Ser Ile
            515                 520                 525

His Ala Arg Leu Ile Gly Ala Tyr Cys Gly Thr Gln Thr Glu Ser Phe
            530                 535                 540

Ser Ser Thr Gly Asn Ser Leu Thr Phe His Phe Tyr Ser Asp Ser Ser
545                 550                 555                 560

Ile Ser Gly Lys Gly Phe Leu Leu Glu Trp Phe Ala Val Asp Ala Pro
            565                 570                 575

Asp Gly Val Leu Pro Thr Ile Ala Pro Gly Ala Cys Gly Gly Phe Leu
            580                 585                 590

Arg Thr Gly Asp Ala Pro Val Phe Leu Phe Ser Pro Gly Trp Pro Asp
            595                 600                 605

Ser Tyr Ser Asn Arg Val Asp Cys Thr Trp Leu Ile Gln Ala Pro Asp
            610                 615                 620

Ser Thr Val Glu Leu Asn Ile Leu Ser Leu Asp Ile Glu Ser His Arg
625                 630                 635                 640
```

```
Thr Cys Ala Tyr Asp Ser Leu Val Ile Arg Asp Gly Asp Asn Asn Leu
                645                 650                 655

Ala Gln Gln Leu Ala Val Leu Cys Gly Arg Glu Ile Pro Gly Pro Ile
            660                 665                 670

Arg Ser Thr Gly Glu Tyr Met Phe Ile Arg Phe Thr Ser Asp Ser Ser
        675                 680                 685

Val Thr Arg Ala Gly Phe Asn Ala Ser Phe His Lys Ser
    690                 695                 700

<210> SEQ ID NO 20
<211> LENGTH: 693
<212> TYPE: PRT
<213> ORGANISM: Human

<400> SEQUENCE: 20

Cys Gly Gly Asn Leu Thr Thr Ser Ser Gly Thr Phe Ile Ser Pro Asn
                5                   10                  15

Tyr Pro Met Pro Tyr Tyr His Ser Ser Glu Cys Tyr Trp Trp Leu Lys
            20                  25                  30

Ser Ser His Gly Ser Ala Phe Glu Leu Glu Phe Lys Asp Phe His Leu
        35                  40                  45

Glu His His Pro Asn Cys Thr Leu Asp Tyr Leu Ala Val Tyr Asp Gly
    50                  55                  60

Pro Ser Asn Ser His Leu Leu Thr Gln Leu Cys Gly Asp Glu Lys
65                  70                  75                  80

Pro Pro Leu Ile Arg Ser Ser Gly Asp Ser Met Phe Ile Lys Leu Arg
                85                  90                  95

Thr Asp Glu Gly Gln Gln Gly Arg Gly Phe Lys Ala Glu Tyr Arg Gln
            100                 105                 110

Thr Cys Glu Asn Val Val Ile Val Asn Gln Thr Tyr Gly Ile Leu Glu
        115                 120                 125

Ser Ile Gly Tyr Pro Asn Pro Tyr Ser Glu Asn Gln His Cys Asn Trp
    130                 135                 140

Thr Ile Arg Ala Thr Thr Gly Asn Thr Val Asn Tyr Thr Phe Leu Ala
145                 150                 155                 160

Phe Asp Leu Glu His His Ile Asn Cys Ser Thr Asp Tyr Leu Glu Leu
                165                 170                 175

Tyr Asp Gly Pro Arg Gln Met Gly Arg Tyr Cys Gly Val Asp Leu Pro
            180                 185                 190

Pro Pro Gly Ser Thr Thr Ser Ser Lys Leu Gln Val Leu Leu Leu Thr
        195                 200                 205

Asp Gly Val Gly Arg Arg Glu Lys Gly Phe Gln Met Gln Trp Phe Val
    210                 215                 220

Tyr Gly Cys Gly Gly Glu Leu Ser Gly Ala Thr Gly Ser Phe Ser Ser
225                 230                 235                 240

Pro Gly Phe Pro Asn Arg Tyr Pro Pro Asn Lys Glu Cys Ile Trp Tyr
                245                 250                 255

Ile Arg Thr Asp Pro Gly Ser Ser Ile Gln Leu Thr Ile His Asp Phe
            260                 265                 270

Asp Val Glu Tyr His Ser Arg Cys Asn Phe Asp Val Leu Glu Ile Tyr
        275                 280                 285

Gly Gly Pro Asp Phe His Ser Pro Arg Ile Ala Gln Leu Cys Thr Gln
    290                 295                 300

Arg Ser Pro Glu Asn Pro Met Gln Val Ser Ser Thr Gly Asn Glu Leu
```

```
                305                 310                 315                 320
Ala Ile Arg Phe Lys Thr Asp Leu Ser Ile Asn Gly Arg Gly Phe Asn
                325                 330                 335
Ala Ser Trp Gln Ala Val Thr Gly Gly Cys Gly Gly Ile Phe Gln Ala
                340                 345                 350
Pro Ser Gly Glu Ile His Ser Pro Asn Tyr Pro Ser Pro Tyr Arg Ser
                355                 360                 365
Asn Thr Asp Cys Ser Trp Val Ile Arg Val Asp Arg Asn His Arg Val
                370                 375                 380
Leu Leu Asn Phe Thr Asp Phe Asp Leu Glu Ser Gln Asp Ser Cys Ile
385                 390                 395                 400
Met Ala Tyr Asp Gly Leu Ser Ser Thr Met Ser Arg Leu Ala Arg Thr
                405                 410                 415
Cys Gly Arg Glu Gln Leu Ala Asn Pro Ile Val Ser Ser Gly Asn Ser
                420                 425                 430
Leu Phe Leu Arg Phe Gln Ser Gly Pro Ser Arg Gln Asn Arg Gly Phe
                435                 440                 445
Arg Ala Gln Phe Arg Gln Ala Cys Gly Gly His Ile Leu Thr Ser Ser
                450                 455                 460
Phe Asp Thr Val Ser Ser Pro Arg Phe Pro Ala Asn Tyr Pro Asn Asn
465                 470                 475                 480
Gln Asn Cys Ser Trp Ile Ile Gln Ala Gln Pro Pro Leu Asn His Ile
                485                 490                 495
Thr Leu Ser Phe Thr His Phe Glu Leu Glu Arg Ser Thr Thr Cys Ala
                500                 505                 510
Arg Asp Phe Val Glu Ile Leu Asp Gly Gly His Glu Asp Ala Pro Leu
                515                 520                 525
Arg Gly Arg Tyr Cys Gly Thr Asp Met Pro His Pro Ile Thr Ser Phe
                530                 535                 540
Ser Ser Ala Leu Thr Leu Arg Phe Val Ser Asp Ser Ser Ile Ser Ala
545                 550                 555                 560
Gly Gly Phe His Thr Thr Val Thr Ala Ser Val Ser Ala Cys Gly Gly
                565                 570                 575
Thr Phe Tyr Met Ala Glu Gly Ile Phe Asn Ser Pro Gly Tyr Pro Asp
                580                 585                 590
Ile Tyr Pro Pro Asn Val Glu Cys Val Trp Asn Ile Val Ser Ser Pro
                595                 600                 605
Gly Asn Arg Leu Gln Leu Ser Phe Ile Ser Phe Gln Leu Glu Asp Ser
                610                 615                 620
Gln Asp Cys Ser Arg Asp Phe Val Glu Ile Arg Glu Gly Asn Ala Thr
625                 630                 635                 640
Gly His Leu Val Gly Arg Tyr Cys Gly Asn Ser Phe Pro Leu Asn Tyr
                645                 650                 655
Ser Ser Ile Val Gly His Thr Leu Trp Val Arg Phe Ile Ser Asp Gly
                660                 665                 670
Ser Gly Ser Gly Thr Gly Phe Gln Ala Thr Phe Met Lys Ile Phe Gly
                675                 680                 685
Asp Ser Ser Val Thr
    690

<210> SEQ ID NO 21
<211> LENGTH: 766
<212> TYPE: PRT
<213> ORGANISM: Human
```

<400> SEQUENCE: 21

```
Met Glu Thr Asp Thr Leu Leu Leu Trp Val Leu Leu Leu Trp Val Pro
  1               5                  10                  15
Gly Ser Thr Gly Asp Ala Ala Gln Pro Ala Arg Arg Ala Val Arg Ser
             20                  25                  30
Leu Val Pro Ser Ser Asp Pro Cys Gly Gly Glu Leu Ser Gly Ala Thr
         35                  40                  45
Gly Ser Phe Ser Ser Pro Gly Phe Pro Asn Arg Tyr Pro Pro Asn Lys
     50                  55                  60
Glu Cys Ile Trp Tyr Ile Arg Thr Asp Pro Gly Ser Ser Ile Gln Leu
 65                  70                  75                  80
Thr Ile His Asp Phe Asp Val Glu Tyr His Ser Arg Cys Asn Phe Asp
                 85                  90                  95
Val Leu Glu Ile Tyr Gly Gly Pro Asp Phe His Ser Pro Arg Ile Ala
            100                 105                 110
Gln Leu Cys Thr Gln Arg Ser Pro Glu Asn Pro Met Gln Val Ser Ser
        115                 120                 125
Thr Gly Asn Glu Leu Ala Ile Arg Phe Lys Thr Asp Leu Ser Ile Asn
    130                 135                 140
Gly Arg Gly Phe Asn Ala Ser Trp Gln Ala Val Thr Gly Gly Cys Gly
145                 150                 155                 160
Gly Ile Phe Gln Ala Pro Ser Gly Glu Ile His Ser Pro Asn Tyr Pro
                165                 170                 175
Ser Pro Tyr Arg Ser Asn Thr Asp Cys Ser Trp Val Ile Arg Val Asp
            180                 185                 190
Arg Asn His Arg Val Leu Leu Asn Phe Thr Asp Phe Asp Leu Glu Ser
        195                 200                 205
Gln Asp Ser Cys Ile Met Ala Tyr Asp Gly Leu Ser Ser Thr Met Ser
    210                 215                 220
Arg Leu Ala Arg Thr Cys Gly Arg Glu Gln Leu Ala Asn Pro Ile Val
225                 230                 235                 240
Ser Ser Gly Asn Ser Leu Phe Leu Arg Phe Gln Ser Gly Pro Ser Arg
                245                 250                 255
Gln Asn Arg Gly Phe Arg Ala Gln Phe Arg Gln Ala Cys Gly Gly His
            260                 265                 270
Ile Leu Thr Ser Ser Phe Asp Thr Val Ser Ser Pro Arg Phe Pro Ala
        275                 280                 285
Asn Tyr Pro Asn Asn Gln Asn Cys Ser Trp Ile Ile Gln Ala Gln Pro
    290                 295                 300
Pro Leu Asn His Ile Thr Leu Ser Phe Thr His Phe Glu Leu Glu Arg
305                 310                 315                 320
Ser Thr Thr Cys Ala Arg Asp Phe Val Glu Ile Leu Asp Gly His His
                325                 330                 335
Glu Asp Ala Pro Leu Arg Gly Arg Tyr Cys Gly Thr Asp Met Pro His
            340                 345                 350
Pro Ile Thr Ser Phe Ser Ser Ala Leu Thr Leu Arg Phe Val Ser Asp
        355                 360                 365
Ser Ser Ile Ser Ala Gly Gly Phe His Thr Thr Val Thr Ala Ser Val
    370                 375                 380
Ser Ala Cys Gly Gly Thr Phe Tyr Met Ala Glu Gly Ile Phe Asn Ser
385                 390                 395                 400
Pro Gly Tyr Pro Asp Ile Tyr Pro Pro Asn Val Glu Cys Val Trp Asn
```

```
                405                 410                 415
Ile Val Ser Ser Pro Gly Asn Arg Leu Gln Leu Ser Phe Ile Ser Phe
                420                 425                 430

Gln Leu Glu Asp Ser Gln Asp Cys Ser Arg Asp Phe Val Glu Ile Arg
            435                 440                 445

Glu Gly Asn Ala Thr Gly His Leu Val Gly Arg Tyr Cys Gly Asn Ser
    450                 455                 460

Phe Pro Leu Asn Tyr Ser Ile Val Gly His Thr Leu Trp Val Arg
465                 470                 475                 480

Phe Ile Ser Asp Gly Ser Gly Ser Gly Thr Gly Phe Gln Ala Thr Phe
                485                 490                 495

Met Lys Ile Phe Gly Asn Asp Asn Ile Val Gly Thr His Gly Lys Val
            500                 505                 510

Ala Ser Pro Phe Trp Pro Glu Asn Tyr Pro His Asn Ser Asn Tyr Gln
        515                 520                 525

Trp Thr Val Asn Val Asn Ala Ser His Val Val His Gly Arg Ile Leu
    530                 535                 540

Glu Met Asp Ile Glu Glu Ile Gln Asn Cys Tyr Tyr Asp Lys Leu Arg
545                 550                 555                 560

Ile Tyr Asp Gly Pro Ser Ile His Ala Arg Leu Ile Gly Ala Tyr Cys
                565                 570                 575

Gly Thr Gln Thr Glu Ser Phe Ser Ser Thr Gly Asn Ser Leu Thr Phe
            580                 585                 590

His Phe Tyr Ser Asp Ser Ser Ile Ser Gly Lys Gly Phe Leu Leu Glu
        595                 600                 605

Trp Phe Ala Val Asp Ala Pro Asp Gly Val Leu Pro Thr Ile Ala Pro
    610                 615                 620

Gly Ala Cys Gly Gly Phe Leu Arg Thr Gly Asp Ala Pro Val Phe Leu
625                 630                 635                 640

Phe Ser Pro Gly Trp Pro Asp Ser Tyr Ser Asn Arg Val Asp Cys Thr
                645                 650                 655

Trp Leu Ile Gln Ala Pro Asp Ser Thr Val Glu Leu Asn Ile Leu Ser
            660                 665                 670

Leu Asp Ile Glu Ser His Arg Thr Cys Ala Tyr Asp Ser Leu Val Ile
        675                 680                 685

Arg Asp Gly Asp Asn Asn Leu Ala Gln Gln Leu Ala Val Leu Cys Gly
    690                 695                 700

Arg Glu Ile Pro Gly Pro Ile Arg Ser Thr Gly Glu Tyr Met Phe Ile
705                 710                 715                 720

Arg Phe Thr Ser Asp Ser Ser Val Thr Arg Ala Gly Phe Asn Ala Ser
                725                 730                 735

Phe His Lys Ser Pro Arg Gly Gly Pro Glu Gln Lys Leu Ile Ser Glu
            740                 745                 750

Glu Asp Leu Asn Ser Ala Val Asp His His His His His
        755                 760                 765

<210> SEQ ID NO 22
<211> LENGTH: 2103
<212> TYPE: DNA
<213> ORGANISM: Human

<400> SEQUENCE: 22
tgtggtggag agctgtctgg ggccacaggc tccttcagca gccccgggtt ccccaacagg      60
tatccaccaa acaaggagtg tatctggtac attaggacgg accccgggag tagcattcag     120
```

-continued

| | |
|---|---|
| ctcaccatcc atgacttcga tgtggagtat cattcaaggt gcaactttga tgtcttggag | 180 |
| atctatggag gccccgattt ccactctccc agaatagccc aactgtgtac ccagagatca | 240 |
| cctgagaacc ccatgcaggt ctccagcact ggaaatgagc tagcaattcg attcaagacc | 300 |
| gacttgtcca taaatgggag aggcttcaat gcgtcatggc aagcagtcac tggaggttgt | 360 |
| ggtgggattt tccaggctcc cagtggagag atacattctc caaattaccc cagtccttat | 420 |
| aggagcaaca cagactgttc ttgggtcatt cgggttgaca gaaatcatcg tgttctcttg | 480 |
| aacttcactg actttgatct tgaatcacaa gactcttgta ttatggcata cgatggctta | 540 |
| agctccacaa tgtcccgcct tgccaggacg tgtggaaggg agcagctggc taaccccatc | 600 |
| gtctcctcag gaaacagcct cttcttgaga tttcagtctg gcccttccag acagaacaga | 660 |
| ggcttccgag ctcaattcag gcaagcctgc ggaggccaca tcctcaccag ctcatttgat | 720 |
| actgtttcct ctccacggtt ccctgccaat tatccaaaca atcagaactg cagctggatc | 780 |
| attcaagcgc aacctccatt aaatcatatc accctctctt ttacccactt tgaacttgaa | 840 |
| agaagcacaa cgtgtgcacg tgactttgta gaaattttgg atggcggcca cgaagacgcg | 900 |
| cccctccgag gccgttactg tggcaccgac atgccccatc ctatcacatc cttcagcagc | 960 |
| gccctgacgc tgagattcgt ctctgattct agcatcagtg ctgggggttt ccacaccacg | 1020 |
| gtcaccgcat cagtgtcggc ttgtggtgga acgttctaca tggctgaagg catcttcaac | 1080 |
| agccctggct acccagacat ttatccccct aatgtggaat gtgtctggaa catcgtcagt | 1140 |
| tcccctggca accggctcca gctgtctttt atatctttcc agttggaaga ctctcaggac | 1200 |
| tgcagcagag attttgtgga gatccgtgaa ggaaatgcca cgggtcactt ggtgggacga | 1260 |
| tactgtggaa actccttccc tctcaattat tcttccatcg ttggacatac cctgtgggtc | 1320 |
| agatttatct cagatggttc tggcagcggc acgggcttcc aggccacatt tatgaagata | 1380 |
| tttggcaatg ataatattgt gggaactcat gggaaagtcg cctctccttt ctggcctgaa | 1440 |
| aactacccac ataactccaa ttaccaatgg acagtaaatg tgaatgcatc tcacgttgtc | 1500 |
| catggtagaa tcttggagat ggacatagaa gaaatacaaa actgctatta tgacaaatta | 1560 |
| aggatctatg atgggcctag cattcacgcc cgcctaattg gagcttactg tggtacccag | 1620 |
| actgaatctt tcagctccac tggaaattct ttgacatttc atttttactc cgactcttca | 1680 |
| atctcaggga agggattcct tctggagtgg tttgcagtgg atgcacctga tggtgtttta | 1740 |
| cctaccattg ctccaggtgc ttgtggtggc ttcctgagga cgggagatgc acccgtgttt | 1800 |
| ctcttctccc cgggctggcc tgacagttac agtaatagag tggactgtac gtggctcatc | 1860 |
| caggctcccg actctaccgt ggaactcaac attctttccc tggacattga atctcaccga | 1920 |
| acgtgtgcct atgatagcct tgtgatacga gatggagata ataacttggc ccagcagcta | 1980 |
| gcagttctct gtggcagaga gatccctggg cccatccggt ctactggaga gtacatgttc | 2040 |
| atccgcttca cctcggactc cagtgtaacc agggcaggct tcaatgcatc ctttcacaag | 2100 |
| agc | 2103 |